US012133833B2

(12) United States Patent
Calvin

(10) Patent No.: US 12,133,833 B2
(45) Date of Patent: *Nov. 5, 2024

(54) MEDICATION VERIFICATION METHOD AND SYSTEM

(71) Applicant: Express Scripts Strategic Development, Inc., St. Louis, MO (US)

(72) Inventor: Kristine Calvin, Troy, IL (US)

(73) Assignee: Express Scripts Strategic Development, Inc., St. Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 18/386,850

(22) Filed: Nov. 3, 2023

(65) Prior Publication Data

US 2024/0058220 A1   Feb. 22, 2024

Related U.S. Application Data

(63) Continuation of application No. 18/124,672, filed on Mar. 22, 2023, now Pat. No. 11,844,751, which is a (Continued)

(51) Int. Cl.
*A61J 7/00* (2006.01)
*A61J 1/03* (2023.01)
(Continued)

(52) U.S. Cl.
CPC .............. *A61J 7/0076* (2013.01); *A61J 1/03* (2013.01); *A61J 7/0084* (2013.01);
(Continued)

(58) Field of Classification Search
CPC ........ A61J 7/0076; A61J 1/03; A61J 2205/10; A61J 2205/30; A61J 1/1412; A61J 7/0084;
(Continued)

(56) References Cited

U.S. PATENT DOCUMENTS 5,720,154 A * 2/1998 Lasher ..................... G07F 5/18
53/411
6,640,159 B2   10/2003 Holmes
(Continued)

FOREIGN PATENT DOCUMENTS

CN    105723382 B    12/2019

*Primary Examiner* — Michael Collins
(74) *Attorney, Agent, or Firm* — Dickinson Wright PLLC

(57) ABSTRACT

A medication dispensing system includes an automated dispensing device that includes cells with electronically activated locks. The device is configured to detect when medication counts in the cells fall below predetermined thresholds. The system further includes a plurality of first electronic devices that are associated with some of the cells and that have imagers. In response to any of the medication counts in the cells being below the predetermined threshold, the automated dispensing device is configured to automatically send a replenishment needed notification to the first electronic device associated with the cell. That first electronic device is configured to transmit a picture of a medication to a second electronic device. In response to a positive verification by a user of the second electronic device that the medication in the picture is the correct medication, the second electronic device is configured to transmit an unlock signal to the automated dispensing device.

20 Claims, 15 Drawing Sheets

Related U.S. Application Data continuation of application No. 17/837,584, filed on Jun. 10, 2022, now Pat. No. 11,633,331, which is a continuation of application No. 17/064,735, filed on Oct. 7, 2020, now Pat. No. 11,389,378.

(51) Int. Cl.
| | |
|---|---|
| *A61J 1/14* | (2023.01) |
| *G06F 3/0482* | (2013.01) |
| *G06K 7/14* | (2006.01) |
| *G06T 7/00* | (2017.01) |
| *G16H 20/13* | (2018.01) |
| *G16H 40/20* | (2018.01) |
| *G16H 40/63* | (2018.01) |
| *G16H 50/70* | (2018.01) |
| *G16H 70/40* | (2018.01) |
| *H04N 7/18* | (2006.01) |

(52) U.S. Cl.
CPC ......... *G06F 3/0482* (2013.01); *G06K 7/1413* (2013.01); *G06K 7/1417* (2013.01); *G06T 7/0014* (2013.01); *G16H 20/13* (2018.01); *G16H 40/20* (2018.01); *G16H 40/63* (2018.01); *G16H 50/70* (2018.01); *G16H 70/40* (2018.01); *H04N 7/183* (2013.01); *A61J 1/1412* (2013.01); *A61J 2205/10* (2013.01); *A61J 2205/30* (2013.01); *G06T 2200/24* (2013.01); *G06T 2207/20092* (2013.01); *G06T 2207/30004* (2013.01)

(58) Field of Classification Search
CPC ........ G16H 20/13; G16H 40/63; G16H 50/70; G16H 70/40; G16H 40/20; G06K 7/1413; G06K 7/1417; G06T 7/0014; G06T 2200/24; G06T 2207/30004; G06T 2207/20092; G06F 3/0482; H04N 7/183
See application file for complete search history.

(56) References Cited

U.S. PATENT DOCUMENTS

| | | | |
|---|---|---|---|
| 7,058,584 B2 | 6/2006 | Kosinski | |
| 8,141,330 B2 * | 3/2012 | Henkel | .................. B65B 5/103 53/500 |
| 8,374,887 B1 | 2/2013 | Alexander | |
| 8,775,198 B2 * | 7/2014 | Wiener | .................. G16H 20/10 705/2 |
| 9,779,217 B2 * | 10/2017 | Jordan | .................. G06Q 10/087 |
| 9,886,751 B2 | 2/2018 | Jacobs | |
| 9,962,316 B2 | 5/2018 | Latorraca | |
| 10,037,646 B2 | 7/2018 | Heffron | |
| 10,120,982 B2 | 11/2018 | Jordan | |
| 10,387,622 B2 | 8/2019 | Hartlaub | |
| 11,389,378 B1 * | 7/2022 | Calvin | .................. A61J 7/0076 |
| 11,633,331 B2 * | 4/2023 | Calvin | .................. G16H 40/20 221/13 |
| 11,844,751 B2 * | 12/2023 | Calvin | .................. G06T 7/0014 |
| 2003/0179287 A1 | 9/2003 | Kozic | |
| 2005/0096785 A1 * | 5/2005 | Moncrief | .............. G06Q 10/08 700/241 |
| 2012/0101847 A1 * | 4/2012 | Johnson | .................. G16H 10/60 705/2 |
| 2016/0110518 A1 | 4/2016 | Louie | |
| 2016/0132662 A1 | 5/2016 | Paradissis | |
| 2017/0076066 A1 | 3/2017 | Adams | |
| 2018/0235843 A1 | 8/2018 | Latorraca | |
| 2020/0016039 A1 | 1/2020 | Boutin | |
| 2021/0313031 A1 * | 10/2021 | Samples | ................ G16H 70/40 |

* cited by examiner

| HOME | | | | |
|---|---|---|---|---|
| REPLENISHMENT QUEUE | HVF > REPLENISHMENT QUEUE | | | |
| ASSIGNED REPLENISHMENT (1) | TOWER/CELL | PRIORITY | TIME WAITING | DRUG |
| | < 1611 | 1 | 12 MINUTES | SYNTHROID 0.05MG TABLET | SELECT |
| | < 1101 | 5 | 4 MINUTES | OMEPRAZOLE DR 20MG CAP | SELECT |
| | < 1410 | 10 | 33 SECONDS | TERAZOSIN HCL 2MG CAPS | SELECT |

MEDICATION VERIFICATION METHOD AND SYSTEM

CROSS REFERENCE TO RELATED APPLICATIONS

This application is a continuation of U.S. application Ser. No. 18/124,672 filed on Mar. 22, 2023; said application is a continuation of U.S. application Ser. No. 17/837,584 filed on Jun. 10, 2022 and issued as U.S. Pat. No. 11,633,331 on Apr. 25, 2023; said application Ser. No. 17/837,584 is a continuation of U.S. application Ser. No. 17/064,735, which was filed Oct. 7, 2020 and issued on Jul. 19, 2022 as U.S. Pat. No. 11,389,378. The entire disclosures of said applications are incorporated herein by reference.

BACKGROUND OF THE INVENTION

1. Field of the Invention

The present invention is related generally to high volume filling center pharmacy. More specifically, the present invention is related to a system in a high volume filling center, which allows medications in the high volume filling center to be restocked in a more efficient manner.

2. Related Art

A high volume pharmacy may process and fill a large number of prescriptions and prescription orders using one or more automated systems. One such automated system is a high volume filler, which can automatically dispense measured quantities of pills from respective cells into appropriate containers that are then individually sent to customers. It is of significant importance that the medications, which are placed into the cells, are accurate in order to ensure that each user receives the correct medications.

SUMMARY OF THE INVENTION AND ADVANTAGES

An aspect of the present disclosure is related to a method of replenishing a medication in an automatic medication dispensing device for filling a plurality of containers with the medications. The method includes the step of preparing the automated dispensing device. The automated dispensing device includes a plurality of cells containing and associated with medications to be dispensed to the containers. The cells are locked by a lock that can be electronically activated. The method proceeds with determining that a medication count in a first cell of the plurality of cells is below a predetermined threshold. The method continues with the step of imaging a medication with a first electronic device to produce an image. The method proceeds with the step of transmitting the image of the medication from the first electronic device to a second electronic device that is remote from the first electronic device. The method continues with the step of comparing the medication in the image to a known medication associated with the first cell to determine if the medication in the picture is the correct medication for replenishing the first cell. The method proceeds with the step of transmitting an unlock signal from the second electronic device to the automated dispensing device to unlock the first cell only in response to a positive determination that the medication in the image is the correct type of medication for replenishing the first cell. The method continues with the step of unlocking the first cell in response to the automated dispensing device receiving the unlock signal from the second electronic device. The method proceeds with the step of replenishing the first cell with the medication.

In an embodiment, the first electronic device is a technician device that is mobile and is operated by a technician on location at the automated dispensing device, and the second electronic device is a pharmacist device that is operated by a pharmacist.

In an embodiment, the image is a photograph, and the method further includes the step of displaying the photograph of the medication on the pharmacist device along with a photograph of the medication associated with the first cell.

In an embodiment, the method further includes the steps of photographing a door of the first cell with the technician device and transmitting a picture of the door from the technician device to the pharmacist device. The step of transmitting the unlock signal from the pharmacist device to the automated dispensing device is also only in response to a positive verification that the picture of the door shows the first cell.

In an embodiment, the method further includes the steps of photographing a medication container that contains the medication with the technician device and transmitting a picture of the medication container to the pharmacist device. The step of transmitting the unlock signal from the pharmacist device to the automated dispensing device is also only in response to a positive verification that the picture of the medication container shows the correct medication container for replenishing the first cell.

In an embodiment, the method further includes the step of displaying all of the picture of the medication, the picture of the door, the picture of the medication container, and a picture of the medication associated with the first cell in a single user interface on the pharmacist device.

In an embodiment, the method further includes the step of storing the pictures of the medication, the door, and the medication container in a memory.

In an embodiment, prior to the step of replenishing the first cell with the medication, the method further includes the steps of opening the first cell, scanning a code on an inside of the cell, verifying the first cell, and only unlocking the first cell in response to the first cell being verified.

In an embodiment, the step of verifying the first cell is performed by the technician device.

Another aspect of the present disclosure is related to a medication dispensing system. The medication dispensing system includes an automated dispensing device that includes a plurality of cells that can be individually and electronically locked and unlocked. Each of the cells is able to contain a plurality of medications. The automated dispensing device is configured to determine a medication count in each of the cells. The automated dispensing device is also configured to detect when the medication count in each of the cells falls below a predetermined threshold. The medication dispensing system further includes a plurality of first electronic devices. Each of the first electronic devices includes an imager and is in electrical communication with the automated dispensing device and is associated with a plurality of the cells of the automated dispensing device. In response to the automated dispensing device detecting that any of the medication counts in the plurality of cells is below the predetermined threshold, the automated dispensing device is configured to automatically send a replenishment needed notification to the one of the first electronic devices associated with the cell. In response to receiving a replenishment needed notification, each of the first electronic devices is configured to transmit a picture of a medication to a second electronic device. In response to a positive verification by a user of the second electronic device that the medication in the picture is the correct medication to replenish the cell with the medication count below the predetermined threshold, the second electronic device is configured to transmit an unlock signal to the automated dispensing device to unlock the cell.

In an embodiment, each of the first electronic devices is a technician device for use by a technician, and the second electronic device is a pharmacist device for use by a pharmacist.

In an embodiment, each of the technician devices includes a display screen and is configured to display a first graphical user interface including the pictures taken with the camera of the technician device prior to the pictures being transmitted to the pharmacist device, and the first graphical user interface includes a manually selectable option to allow the technician to re-take any of the pictures.

In an embodiment, the pharmacist device includes a display screen that is configured to display a manually selectable queue of technician devices awaiting verification.

In an embodiment, the queue of technician devices awaiting verification are organized according to a priority score that is based on the urgency to replenish the respective cells those technician devices are associated.

In an embodiment, each of the cells has a door that can be opened and closed, and an outer surface of each cell includes an image of the medication contained inside the cell.

Yet another aspect of the present disclosure is related to a method of replenishing an automatic medication dispenser. The method includes the step of preparing a plurality of cells. Each cell contains a plurality of medications to be dispensed into containers. The method proceeds with the step of associating a plurality of technician devices with the plurality of cells such that each cell is associated with at least one of the technician devices. The technician devices are in electrical communication with a pharmacist device. The method continues with the step of receiving a notification on a first technician device of the plurality of technician devices that a first cell requires replenishment. The method proceeds with the step of transmitting pictures of a first replenishment medication and of the first cell from the first technician device to the pharmacist device. The method continues with the step of receiving a notification on a second technician device of the plurality of technician devices that a second cell requires replenishment. The method proceeds with the step of transmitting pictures of a second replenishment medication and of the second cell from the second technician device to the pharmacist device. The method continues with the step of displaying a queue containing the first and second technician devices on the pharmacist device. The method proceeds with the step of selecting one of the first and second cells with the pharmacist device. The method continues with the step of displaying the pictures from the selected one of the technician devices on the pharmacist device for approval by a pharmacist. The method proceeds with the step of transmitting an unlock signal from the pharmacist device to the first or second cell to unlock a door of the first or second cell in response to approval of the pictures by the pharmacist on the pharmacist device.

In an embodiment, the queue organizes the first and second technician devices according to a priority score.

In an embodiment, the priority score is based on urgency that the cells requiring replenishment will run out of medications.

In an embodiment, an external device including a memory is provided, and the method further includes the step of storing the pictures of the first and second replenishment medications and of the first and second cells in the memory of the external device.

In an embodiment, the method further includes the steps of opening the door of the first or second cell; scanning a code on an inside of the door; and verifying that the code on the inside of the door is the correct code associated with the first cell.

BRIEF DESCRIPTION OF THE DRAWINGS

These and other features and advantages of the invention will become more readily appreciated when considered in connection with the following description of the presently preferred embodiments, appended claims and accompanying drawings, in which:

FIG. 10 illustrates a first graphical user interface;

FIG. 11 also illustrates the first graphical user interface after an additional picture has been taken;

FIG. 13 illustrates a second graphical user interface;

FIG. 14 illustrates a third graphical user interface; and

DETAILED DESCRIPTION OF THE ENABLING EMBODIMENTS

At times, handling medication units must be verified by a licensed pharmacist, e.g., using an electronic device associated with the pharmacist. In many instances, a pharmacist who has expert knowledge of the medications must personally verify all medications before they are loaded into the respective cells of the high volume filler. For example, in a high volume filler, the pharmacist must physically be present at the high volume filler and manually unlock a cell with a prior to adding medications to that cell. The present disclosure provides systems and methods for a pharmacist to remotely or virtually verify drug fill via a display on a monitor remote from the container with the drug fill.

Figure 1:
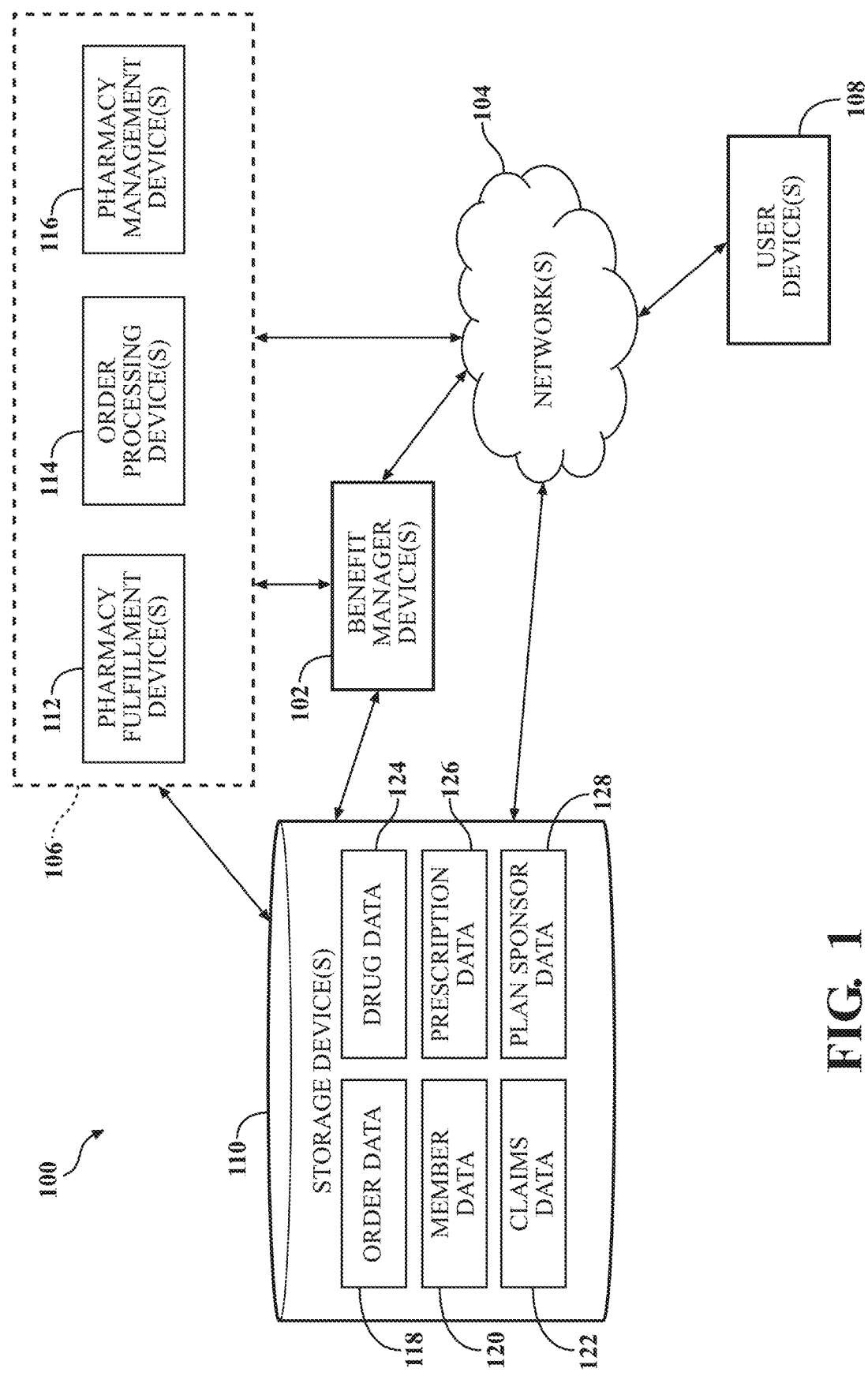
FIG. 1 is a block diagram of an example system according to an example embodiment.

FIG. 1 is a block diagram of an example implementation of a system 100, according to an example embodiment. While the system 100 is generally described as being deployed in a high volume pharmacy or fulfillment center (e.g., a mail order pharmacy, a direct delivery pharmacy, an automated pharmacy, multiple package delivering center, and the like), the system 100 and/or components thereof may otherwise be deployed (e.g., in a lower volume pharmacy).

A high volume pharmacy may be a pharmacy that is capable of filling prescriptions automatically, mechanically, manually, or a combination thereof. The system 100 may include a benefit manager device 102, a pharmacy device 106, and a user device 108, which may communicate with each other directly and/or over a network 104. The system may also include a storage device 110.

The benefit manager 102 is a device operated by an entity that is at least partially responsible for creation and/or management of the pharmacy or drug benefit. While such an entity operating the benefit manager device 102 is typically a pharmacy benefit manager (PBM), other entities may operate the benefit manager device 102 either on behalf of themselves, the PBM, another entity, or other entities. For example, the benefit manager device 102 may be operated by a health plan, a retail pharmacy chain, a drug wholesaler, a data analytics or other type of software-related company, or the like. In some embodiments, a PBM that provides the pharmacy benefit may also provide one or more than one additional benefits including a medical or health benefit, a dental benefit, a vision benefit, a wellness benefit, a radiology benefit, a pet care benefit, an insurance benefit, a long term care benefit, a nursing home benefit, and the like. The PBM may, in addition to its PBM operations, operate one or more than one pharmacy. The pharmaceutical vending machines or kiosks, and the like.

Some of the operations of the PBM that operates the benefit manager device 102 may include the following activities and processes. A member (or a person on behalf of the member) of a pharmacy benefit plan administered by or through the PBM attempts to obtain a prescription drug at a retail pharmacy location (e.g., a location of a physical store) from a pharmacist or a pharmacist technician. The member may also attempt to obtain the prescription drug through mail order drug delivery from a mail order pharmacy location, which may be the high volume pharmacy system 100. In some embodiments, the member may also attempt to obtain the prescription drug directly or indirectly through the use of a machine, such as a kiosk, vending unit, mobile electronic device, or a different type of mechanical electrical, electronic communication device, and/or computing device. Such a machine may be filled with the prescription drug in prescription packaging, which may include multiple prescription components, by the high volume pharmacy system 100.

The member may have a copayment for the prescription drug that reflects an amount of money that the member is responsible to pay the pharmacy for the prescription drug. The money paid by the member to the pharmacy may come from personal funds of the member, a health savings account (HAS) of the member or the member's family, a health reimbursement arrangement (HRA) of the member or the member's family, a flexible spending account (FSA) of the member or the member's family, or the like. In some instances, an employer of the member may directly or indirectly fund or reimburse the member for the copayments.

The amount of the co-pay required form the member may vary with different pharmacy benefit plans having different plan sponsors or clients and/or prescription drugs. The member's copayment may be based on a flat copayment (e.g., $10), co-insurance (e.g., 10%), and/or a deductible (e.g., for first $500 of annual prescription drug expenses) for certain prescription drugs, certain types and/or classes of prescription drugs, and/or all prescription drugs. The copayment may be stored in the storage 110 or determined by the benefit manager device 102.

In some instances, the member may not pay the copayment or may only pay a portion of the copayment for the prescription drug. For example, if the usual and customary cost for a generic version of a prescription drug is $4, and the member's flat copayment is $20 for the prescription drug, the member may only be required to pay $4 to receive the prescription drug. In another example involving a worker's compensation claim. No copayment may be due by the member for the prescription drug.

In addition, copayments may also vary based on different delivery channels used for the prescription drug to be received by the member. For example, the copayment for receiving the prescription drug from a mail order pharmacy location may be less than the copayment for receiving the prescription drug from a retail pharmacy location.

In conjunction with receiving the copayment (if any) from the member and dispensing the prescription drug to the member, the pharmacy submits a claim to the PBM for the prescription drug. After receiving the PBM (e.g., through the benefit manager device 102) may perform certain adjudication operations including verifying eligibility of the member, identifying and/or reviewing an applicable formulary for the member to determine any appropriate copayment, coinsurance, and deductible for the prescription drug, and performing a drug utilization review (DUR) on the member. The PBM provides a response to the pharmacy (e.g., from the benefit manager device 102 to the pharmacy device 106) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated.

The aforementioned adjudication operations generally occur before the copayment is received and the prescription drug is dispensed. However, in some instances these operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be determined at least partially based on the type(s) of pharmacy network in which the pharmacy is included. Other factors may also be used to determine the amount in addition to the type of pharmacy network. For example, if the member pays the pharmacy for the prescription drug without the prescription drug benefit provided by the PBM (e.g., by paying cash without use of the prescription drug benefit or by use of a so-called pharmacy discount card offering other negotiated rates), the amount of money paid by the member may be different than when the member uses prescription or drug benefit. In some embodiments, the amount of money received by the pharmacy for dispensing the prescription drug and for the prescription drug itself may be higher than when the member uses the prescription or drug benefit. Some or all of the foregoing operations may be performed by executing instructions stored on the benefit manager device 102 and/or an additional device.

Examples of the network 104 include Mobile Communications (GSM) network, a code division multiple access (CDMA) network, $3^{rd}$ Generation Partnership Project (3GPP), an Internet Protocol (IP) network, a Wireless Application Protocol (WAP) network, a WiFi network, or an IEEE 802.11 standards network, as well as various combinations thereof. The network 104 may include an optical network. The network 104 may be a local area network or a global communication network, such as the Internet. In some embodiments, the network 104 may include a network dedicated to prescription e-orders, e.g., a prescribing network such as the electronic prescribing network operated by Surescripts of Arlington, Virginia.

Moreover, although the system shows a single network 104, multiple networks can be used. The multiple networks may communicate in series with each other to link the devices 102, 106-110 or in parallel to link the devices 102, 106-110.

The pharmacy device 106 may include an order processing device 114, a pharmacy manager device 116, and a pharmacy fulfillment device 112 in communication with each other directly and/or over the network 104.

The order processing device 114 may receive information regarding filling prescriptions and may direct an order component to one or more than one of the devices of the pharmacy fulfillment device 112 at a pharmacy. The pharmacy fulfillment device 112 may fulfill, dispense, aggregate, and/or pack the order components of the prescription drugs in accordance with one or more than one of the prescription orders directed by the order processing device 114. The order processing device 114 may be deployed in the system 100, or may otherwise be used.

In general, the order processing device 114 is a device located within or otherwise associated with the pharmacy to enable fulfillment of a prescription and dispensing prescription drugs by the pharmacy fulfilment device 112. In some embodiments, the order processing device 114 may be an external device separate from the pharmacy and communicate with other devices located within the pharmacy.

For example, the external order processing device 114 may communicate with an internal order processing device 114 and/or other devices located within the system 100. In some embodiments, the external order processing device 114 may have limited functionality (e.g., as operated by a patient requesting fulfillment of a prescription drug), while the internal pharmacy order processing device 114 may have greater functionality (e.g., as operated by a pharmacist).

The order processing device 114 may track the prescription order as it is fulfilled by the pharmacy fulfillment device 112. The prescription order may include one or more than one prescription drugs to be filled by the pharmacy. The order processing device 114 may make pharmacy routing decisions and/or order consolidation decisions for the particular prescription order. The pharmacy routing decisions may include what device(s) in the pharmacy are responsible for filling or otherwise handling certain portions of the prescription order. The order consolidation decisions include whether portions of one prescription order or multiple prescription orders should be shipped together for a patient or a patient family. The order processing device 114 may also track and/or schedule literature or paperwork associated with each prescription order or multiple prescription orders that are being shipped together.

The pharmacy management device 116 may enable and/or facilitate management and operations in a pharmacy. For example, the pharmacy management device 116 may provide functionality to enable receipt and processing of prescription drug claims, management of pharmacy personnel, management of pharmaceutical and non-pharmaceutical products, track products in the pharmacy, record workplace incidents involve personnel and products, and the like. In some embodiments, the order processing device 114 may operate in combination with the pharmacy management device 116.

In some embodiments, the pharmacy management device 116 may be a device associated with a retail pharmacy location (e.g., exclusive pharmacy location, a grocery store with a retail pharmacy, or a general sales store with a retail pharmacy) or other type of pharmacy location at which a member attempts to obtain a prescription. The pharmacy management device 116 may be utilized by the pharmacy to submit the claim to the PBM (e.g., through the benefit management device 102) for adjudication.

In some embodiments, the pharmacy management device 116 may enable information exchange between the pharmacy and the PBM, for example, to allow the sharing of member information such as drug history, and the like, that may allow the pharmacy to better service a member (e.g., by providing more informed therapy consultation and drug interaction information, etc.). In some embodiments, the benefit manager 102 may track prescription drug fulfillment and/or other information for patients that are not members or have not identified themselves as members, at the time (or in conjunction with the time) in which they seek to have a prescription filled at a pharmacy.

The pharmacy fulfillment devices 112, the order processing device, and/or the pharmacy management device 116 may include circuitry, a processor, a memory to store data and instructions, and communication functionality. These devices 112-116, in some embodiments are dedicated to performing processes, methods and/or instructions described herein. Other types of electronic devices specifically configured to implement with the processes, methods and/or instructions described herein may also be used.

In some embodiments, at least some functionality of the order processing device 114 may be included in the pharmacy management device 116 may include circuitry, a processor, a memory to store data and instructions, and communication functionality. These devices 112-116, in some embodiments, are dedicated to performing processes, methods and/or instructions described herein. Other types of electronic devices specifically configured to implement with the processes, methods and/or instructions described herein may also be used.

In some embodiments, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (e.g., by utilizing a local storage) and/or through the network 104 (e.g., by utilizing a cloud configuration or software as a service, etc.) with the storage 110.

The user device 108 is used by a device operator. The device operator may be a user (e.g., an employee, a contractor, a benefit member, a patient of the pharmacy, or the like) associated with the system 100. Other device operators may also operate the user device 108. In some embodiments, the user device 108 may enable the device operator to attend to pharmacy operations in a convenient manner (e.g., remote from a pharmacy). In some embodiments, the user device 108 may enable the device operator to receive information about pharmacy processes, prescription drug fulfillment status, and the like.

The user device 108 may be a stand-alone device that solely provides at least some of the functionality of the methods and systems, or may be a multi-use device that has functionality outside off analysis of the methods and systems. Examples of the user device 108 include a set-top box (STB), a receiver card, a mobile telephone, a personal digital assistant (PDA), a display device, a portable gaming unit, a computing system, and the like. Other devices, however, may also be used. In some embodiments, the computing system may include a mobile computing device. For example, the user device 108 may include a mobile electronic device, such as an iPhone or iPad by Apple, Inc., and mobile electronic devices powered by Android by Google, Inc. The user device 108 may also include other computing devices, such as desktop computing devices, notebook computing devices, netbook computing devices, gaming devices, and the like. Other types of electronic devices may also be used.

The storage device 110 may include: a non-transitory storage (e.g., memory, hard disk, CD-ROM, and the like) in communication with the benefit manager device 102, the pharmacy device 106, and/or the user device 108 directly and/or over the network 104. The non-transitory storage may store order data 118, member 120, claims data 122, drug data 124, prescription data 126, and/or plan sponsor 128. Further, the system 100 may include additional devices, which may communicate with each other directly or over the network 104.

The order data 118 may be related to a prescription order. The order data may include the type of the prescription drug (e.g., drug name and strength) and quantity of the prescription drug. The order data 118 may also include data used for completion of the prescription, such as prescription materials and/or the type and/or size of container in which the drug is dispensed or in which is requested to be dispensed. In general, prescription materials include an electronic copy of information regarding the prescription drug for inclusion with or otherwise provided (e.g., via email) in conjunction with the fulfilled prescription. The prescription materials may include electronic information regarding drug interaction warnings, recommended usage possible side effects, expiration date, date of prescribing, or the like. The order data 118 may be used by the pharmacy to fulfill a pharmacy order.

In some embodiments, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (e.g., a prescription bottle and sealing lid, prescription packaging, and the like) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information, such as bar code data read from pallets, bins, trays, carts, and the like used to facilitate transportation of prescriptions within the pharmacy may also be stored as order data 118.

The member data 120 includes information regarding the members associated with the PBM. The information stored as member data 120 may include personal information, personal health information, protected health information, fitness data, health data, web and mobile app activity, and the like. Examples of the member data 120 include name, address, telephone number, e-mail address, prescription drug history, and the like. The member data 120 may include a plan sponsor identifier that identifies the plan sponsor associated with the member and/or a member identifier that identifies the member to the plan sponsor. The member data 120 may also include, by way of example, dispensation preferences such as type of label, type of cap, message preferences, language preferences, or the like.

The member data 120 may be accessed by various devices in the pharmacy to obtain information utilized for fulfillment and shipping of prescription orders. In some embodiments, an external order processing device 114 operated by or on behalf of a member may have access to at least a portion of the member data 120 for review, verification, or other purposes.

In some embodiments, the member data 120 may include information for persons who are patients of the pharmacy but are not members in a pharmacy benefit plan being provided by the PBM. For example, these patients may obtain drugs directly from the pharmacy, through a private label service offered by the pharmacy, or otherwise. In general, the use of the terms member (e.g., of a prescription drug benefit plan) and patient (e.g., of a pharmacy) may be used interchangeably in this disclosure.

The claims data 122 includes information regarding pharmacy claims adjusted by the PBM under a drug benefit program provided by the PBM for one, or more than one, plan sponsor. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility, and the like. Additional information may be included.

In some embodiments, other types of claims beyond prescription drug claims may be stored in the claims data 122. For example, medical claims, dental claims, wellness claims, or other types of health care-related claims for members may be stored as a portion of the claims data.

In some embodiments, the claims data 122 includes claims that identify the members with whom the claims are associated. In some embodiments, the claims data 122 includes claims that have been de-identified (e.g., associated with a unique identifier but not with a particular, identifiable member), aggregated, and/or otherwise processed.

The drug data 124 may include drug name (e.g., technical name and/or common name), other names by which the drug is known by, active ingredients, an image of the drug (e.g., in pill form), and the like. The drug data 124 may include information associated with a single medication or multiple medications.

The prescription data 126 may include information regarding prescriptions that may be issued by prescribers on behalf of patients, who may be members of the pharmacy benefit plan, for example to be filled by a pharmacy. Examples of the prescription data 126 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, and the like.

Figure 2:
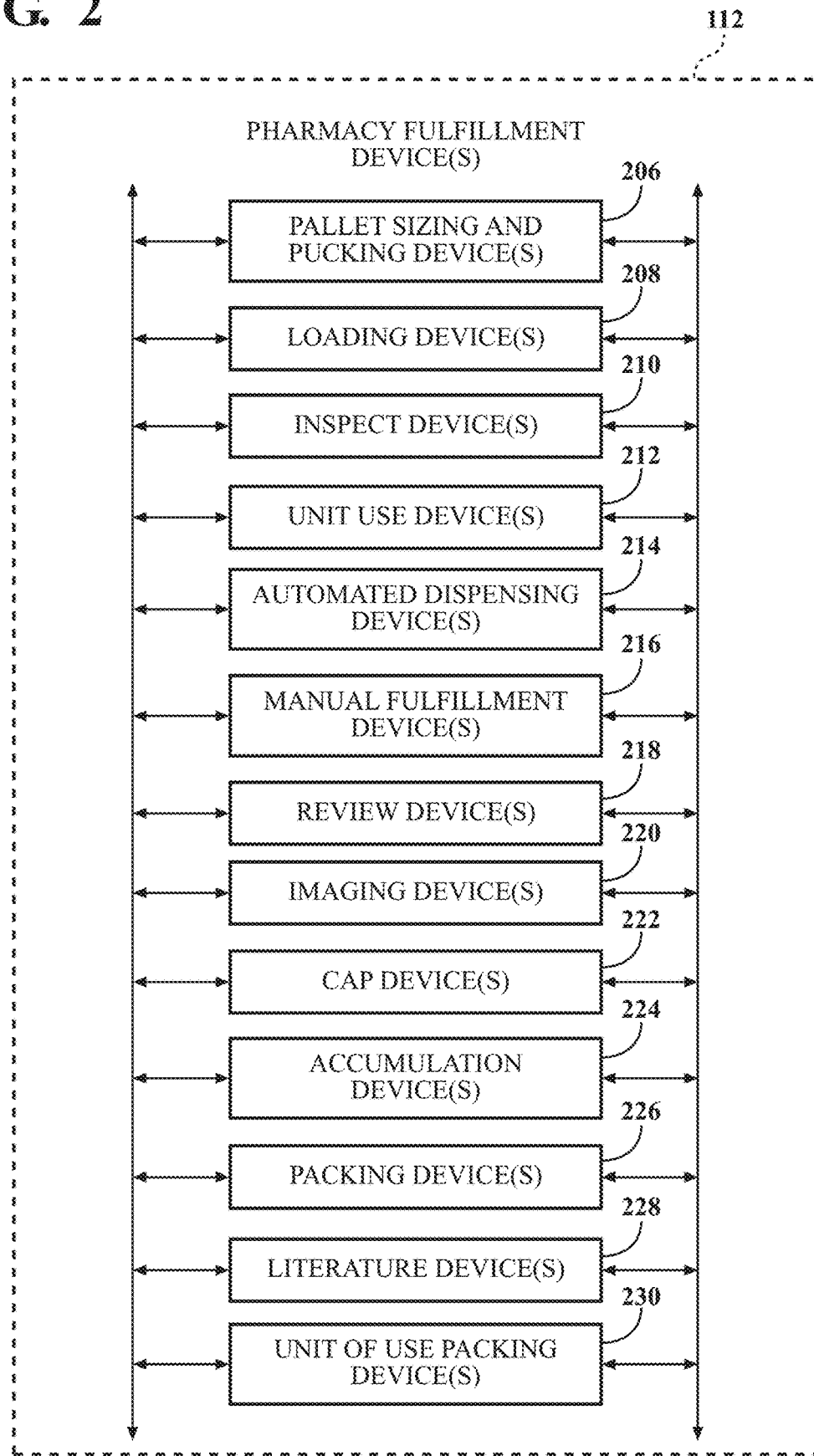
FIG. 2 is a block diagram of an example order processing device that may be deployed within the system of FIG. 1.

FIG. 2 illustrates the pharmacy fulfillment device 112, according to an example embodiment. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device, the order processing device 114, and/or the non-transitory storage 110, directly or over the network 104. Specifically, the pharmacy fulfillment device 112 may include pallet sizing and pucking device(s); loading device(s) 208; inspect device(s) 210, unit of use device(s) 212, automated dispensing device(s) 214, manual fulfillment device(s) 214, review device(s) 218, imaging device(s) 220, cap device(s) 222, accumulation device(s) 224, literature device(s) 228, packing device(s) 226, and unit of use packing device(s) 230. Further, the pharmacy fulfillment device 112 may include additional devices, which may communicate with each other directly or over the network 104.

In some embodiments, operations performed by one or more of these devices 206-230 may be performed sequentially, or in parallel with the operations of devices as may be coordinated by the order processing device 114. In some embodiments, the order processing device 114 tracks a prescription with the pharmacy based on operations performed by one or more than one of the devices 206-230.

In some embodiments, the pharmacy fulfillment device 112 may transport prescription drug containers, for example, between more than one of the devices 206-230 in a high volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism, or the like. In one embodiment, the loading device 208 has robotic arms or pickers to grasp a prescription container and move it to and from a pallet or to and from a puck. The loading device may also print a label that is appropriate for a container that is to be loaded onto the pallet and apply the label to the container. The pallet may be located on a conveyor assembly during these operations (e.g., at the high volume fulfillment center or the like).

The inspect device 210 may verify that containers in a pallet are correctly labeled and in the correct spot on the pallet. The inspect device 210 may scan the label on one or more than one container on the pallet. Labels of containers may be scanned or imaged in full or in part by the inspect device 210. Such imaging may occur after the container has been lifted out of its puck by a robotic arm, picker, or the like, or may be otherwise scanned or imaged while retained in the puck. In some embodiments, images and/or video captured by the inspect device may be stored in the storage device as a portion of the order data 118.

The unit of use device 212 may temporarily store, monitor, label, and/or dispense unit of use products. In general, unit of use products are prescription drug products that may be delivered to a patient or member without being repackaged at the pharmacy. These products may include pills in a container, pills in a blister pack, inhalers, liquids in a spray or other dispensing container, and the like. Prescription drug products dispensed by the unit of use device 212 may be packaged individually or collectively for shipping, or may be shipped in combination with other prescription drugs dispensed by other devices (e.g., in the high volume fulfillment center).

At least some of the operations of the devices 206-230 may be directed by the other processing device 114. For example, the manual fulfillment device 216, the review device 218, the automated dispensing device 214, the packing device 226, and/or another device may receive instructions provided by the order processing device.

The automated dispensing device 214 may include one or more than one device that dispenses prescription drugs or pharmaceuticals into prescription containers in accordance with one or multiple prescription orders. In general, the automated dispensing device 214 may include mechanical and electronic components with, in some embodiments, software and/or logic to facilitate pharmaceutical dispensing that would otherwise be performed in a manual fashion by a pharmacist and/or pharmacist technician. For example, the automated dispensing device 214 may include high volume fillers (HVFs) that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high volume fulfillment center.

The manual fulfillment device 216 may provide for manual fulfillment of prescriptions. For example, the manual fulfillment device 216 may receive or obtain a container and enable fulfillment of the container by a pharmacist or pharmacy technician. In some embodiments, the manual fulfillment device 216 provides the filled container to another device in the pharmacy fulfillment devices 112 to be joined with other containers in a prescription order for a patient or member. In general, a manual fulfillment may include operations at least partially performed by a pharmacist or a pharmacy technician. For example, a person may retrieve a supply of the prescribed drug, may make an observation, may count out a prescribed quantity of drugs and place them into a prescription container, or the like. Some portions of the manual fulfillment process may be automated by use of a machine. For example, counting of capsules, tablets, or pills may be at least partially automated (e.g., through use of a pill counter or the like). Prescription drugs dispensed by the manual fulfillment device 216 may be packaged individually or collectively for shipping or may be shipped in combination with other prescription drugs dispensed by other devices in the high volume fulfillment center.

The review device 218 may process prescription containers to be reviewed by a pharmacist for proper pill count, exception handling, prescription verification, and the like. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been cancelled, containers with defects, and the like. In an example embodiment, the manual review may be performed at the manual station.

The imaging device 220 may image containers prior to filling and/or after they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114, and/or stored in the storage device 110 as part of the order data 118.

The cap device 222 may be used to cap or otherwise seal a prescription container. In some embodiments, the cap device 222 may secure a prescription container with a type of cap in accordance with a patient preference (e.g., a preference regarding child resistance, a preference regarding built-in adherence functionality, or the like), a plan sponsor preference, a prescriber preference, or the like. The cap device 222 may also etch a message into the cap or otherwise associate a message into the cap, although this process may be performed by a different device in the high volume fulfillment center.

The accumulation device 224 accumulates various containers of prescription devices in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218, at the high volume fulfillment center. The accumulation device 224 may be used to group the prescription containers prior to shipment to the member or otherwise.

The literature device 228 prints, or otherwise generates, literature to include with prescription drug orders. The literature may be printed on multiple sheets of substrates, such as paper, coated paper, printable polymers, or combinations thereof. The literature printed by the literature device 228 may include information required to accompany the prescription drugs included in a prescription order, relating to prescription drugs in the order, financial information associated with the order (e.g., an invoice or an account statement, or the like).

In some embodiments, the literature device 228 folds or otherwise prepares the literature for inclusion with a prescription drug order (e.g., in a shipping container or the like).

In some embodiments, the literature device 228 that prints the literature may be separate from the literature device that prepares the literature for inclusion with a prescription order. The packing device 226 packages a prescription order in preparation for shipping the order. The packing device 226 may box, bag, or otherwise package the fulfilled prescription order for delivery. The packing device 226 may be a wrap seal device. A wrap seal device deployed as the packing device 226 may be a wrap seal device. A wrap seal device deployed as the packing device 226 may pause before an index; during the pause, one or more bottle, envelope or literature items have been placed within a vacuum pocket of the wrap seal device. After any bottle, envelope, or literature items have been placed in the pocket, the wrap seal device may index; specifically, the vacuum pocket may move forward. In an example embodiment, the forward movement is about the length of a bag (for example, between about 16 and 20 inches).

The packing device 226 may further place inserts (e.g., literature or other papers) into the packaging received from the literature device 228 or otherwise. For example, bulk prescription orders may be shipped in a box, while other prescription orders may be shipped in a bag, which may be a wrap seal bag. The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, sort by zip code, or the like). The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, sort by zip code, or the like). The packing device 226 may include ice or temperature sensitive elements for prescriptions which are to be kept within a temperature range during shipping in order to retain efficacy or otherwise. The ultimate package may then be shipped through postal mail, through a mail order delivery service that ships via ground and/or air (e.g., UPS®, FedEx®, or DHL®, or the like), through delivery service, through a local delivery service (e.g., a courier service), through a locker box at a shipping site (e.g., an Amazon® locker, library locker, a post office box, or the like) or otherwise.

The unit of use packing device 230 packages a unit of use prescription order in preparation for shipping the order.

The pharmacy fulfillment device 112 in FIG. 2 may include single devices 206-230 or multiple devices 206-230 (e.g., depending upon implementation in a pharmacy). The devices 206-230 may be the same type or model of device or may be different device types or models. When multiple devices are present, the multiple devices may be of the same device type or models or may be a different device type or model. The types of devices 206-230 shown in FIG. 2 are example devices. In other configurations of the system 100, lesser, additional, or different types of devices may be included.

Moreover, multiple devices may share processing and/or memory resources. The devices 206-230 may be located in the same area or in different locations. For example, the devices 206-230 may be located in a building or a set of adjoining buildings. The devices 206-230 may be interconnected (e.g., by conveyors), networked, and/or otherwise in contact with one another or integrated with one another (e.g., at the high volume fulfillment center). In addition, the functionality of a device may be split among a number of discrete devices and/or combined with other devices.

Figure 3:
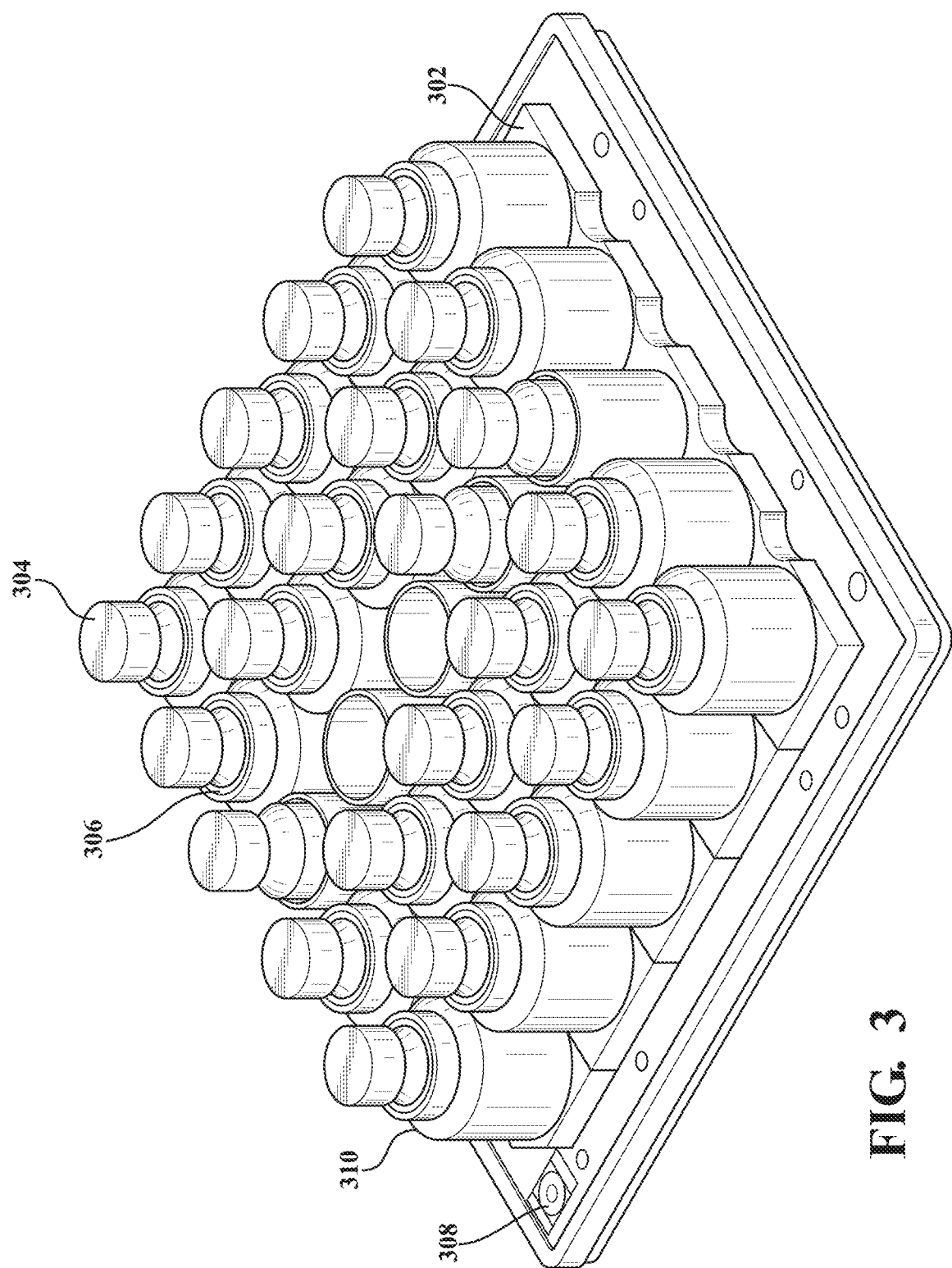
FIG. 3 is a perspective elevation view of a pallet containing a plurality of containers.

FIG. 3 illustrates a pallet 302, according to an example embodiment, which may be used in the pharmacy fulfillment device 112 of the system 100 of FIG. 1. The pallet 302 may be a transport structure for a number of prescription containers 304, and may include a number of cavities 306. While the pallet 302 is shown to include 25 cavities in a five by five cavity row/column configuration, other numbers of categories and/or cavity configurations of varying shapes, sizes, and/or dimensions may be used. In some embodiments, the pallet 302 may be substantially square and, in such an embodiment, have a width and length of between approximately 18 inches and 22 inches (e.g., approximately 18 inches, 19 inches, 20 inches, 21 inches, or 22 inches). In some embodiments, the width and/or length may be greater than approximately 22 inches or less than approximately 18 inches.

In an example embodiment, the cavities 306 are spaced on the pallet 302 such that the center point of adjacent cavities 306 is approximately 3 and 4 inches (e.g., approximately 3 inches, 3.25 inches, 3.5 inches, 3.75 inches, or 4 inches). In another example embodiment, the distance between center points of adjacent cavities 306 is more than approximately 4 inches. In yet another example embodiment, the center points of cavities 306 are less than approximately 3 inches apart.

The pallet 302 may be made in whole or in part of metal, such as aluminum. Other suitable materials may be used for the pallet 302, such as plastic. The pallet 302 may be rigid so that the cavities remain in a known location that can be tracked while the pallet 302 moves through the system 100. The pallet 302 may include bumpers.

In some embodiments, other carriers beyond the pallet 302 and/or no carrier may be used to move containers or groups of containers through the system 100.

The pallet 302 may retain one or more than one container 304. A container 304 is generally cylindrical and may be one or a variety of sizes utilized by a pharmacy for fulfillment of a prescription. For example, a pharmacy may have two different sized containers or three different sized containers. Any number of different sized containers may be used with the pallet 302. While the container 304 is generally denoted as being used with the pallet 302, the containers 304 may otherwise be used in the system 100 or in a different system. Shapes beyond cylindrical shapes may be used for the containers 304. Examples of other shapes include regular prisms, elliptical cylinders, and combinations thereof. The receptacle of a puck may be sized to receive and support the outer shape of the container. The containers 304 may be disposed in the pallet 302 such that they are close to one another but do not touch.

The pallet 302 may include a radio-frequency identification (RFID) tag 308. The RFID tag 308 may be an active RFID tag, such as an active RFID tag with a close reading range. In some embodiments, the RFID tag 308 is an active, narrowband, read/write RFID tag.

The RFID tag 308 of a particular pallet 302 may store data (or otherwise facilitate the access of data, e.g., from the database 108) associated with the containers 304 that have been, are, and/or will be placed within the pallet 302, such as the order data, the claims data, the drug data, the prescription data, and/or the plan sponsor data associated with such containers. Other data may be stored by and/or associated with the RFID tag 314, such as the age of the pallet 302, the number of times the pallet 302 has been used to transport containers 304 through the system 100, the number of errors associated with the pallet 302, and the like. The RFID tag 314 may also store the position of individual containers on the pallet 302. In an example embodiment, the RFID tag 308 of the pallet 302, while deployed within an automated dispensing device 212, stores data associated with one or more of the following data fields: (1) container identifiers, (2) identifier of the particular automated dispensing device 212, (3) identifiers of the particular cells from which a particular container will be filled (as described below), (4) container properties (e.g., the status of containers 304 on the pallet 302, such as whether the containers 304 have passed an inspection station and have been identified as containers 304 to be filled in the particular automated dispensing device 212), and (5) the pallet route within the automated dispensing device 212.

The pucks 310 may be used to modify the size of the cavities 306 to allow the pallet 302 to accommodate different sizes of the containers 304.

Figure 4:
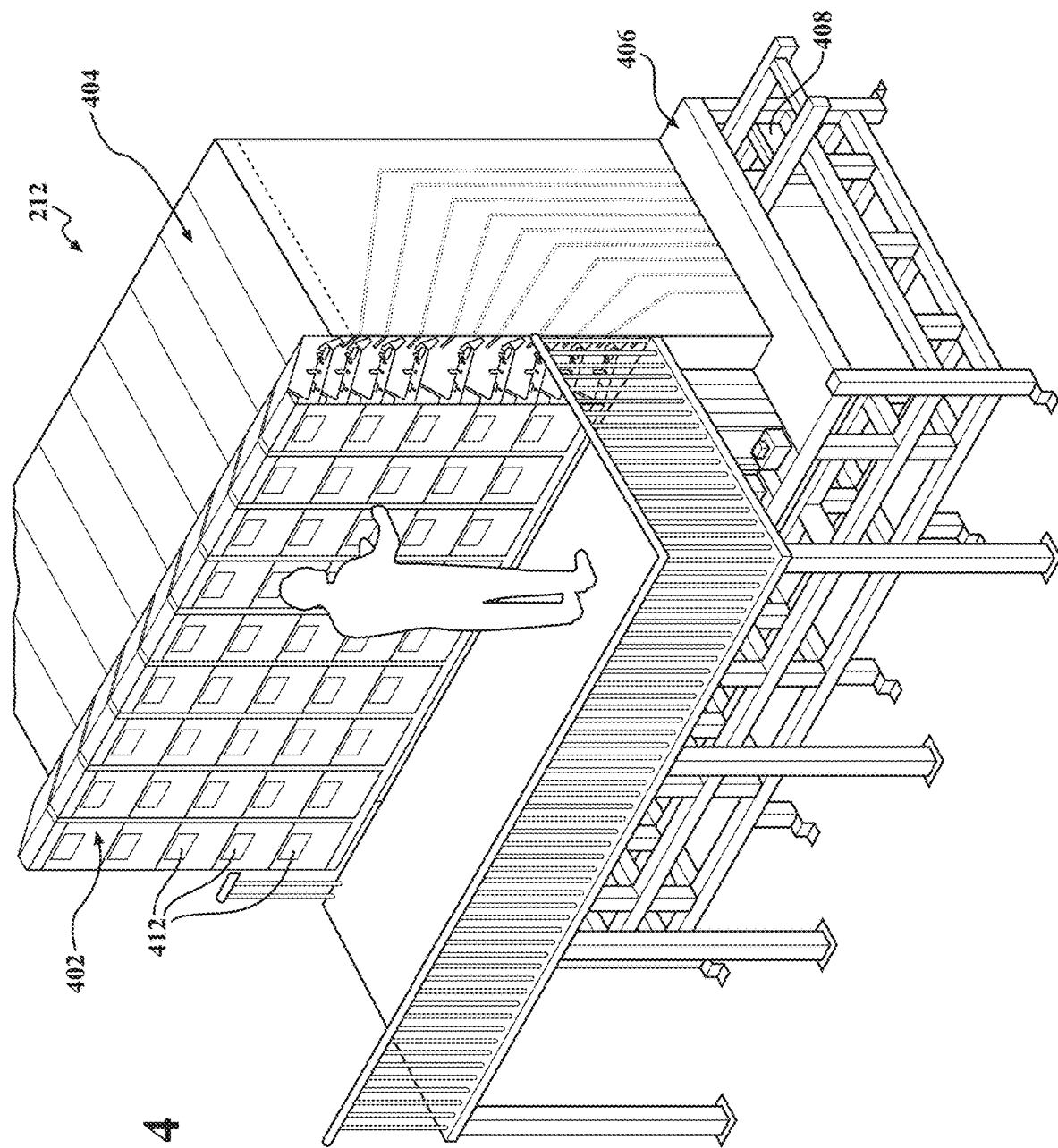
FIG. 4 is a perspective elevation view of a unit of use device that may be deployed within the system of FIG. 1.
Figure 5:
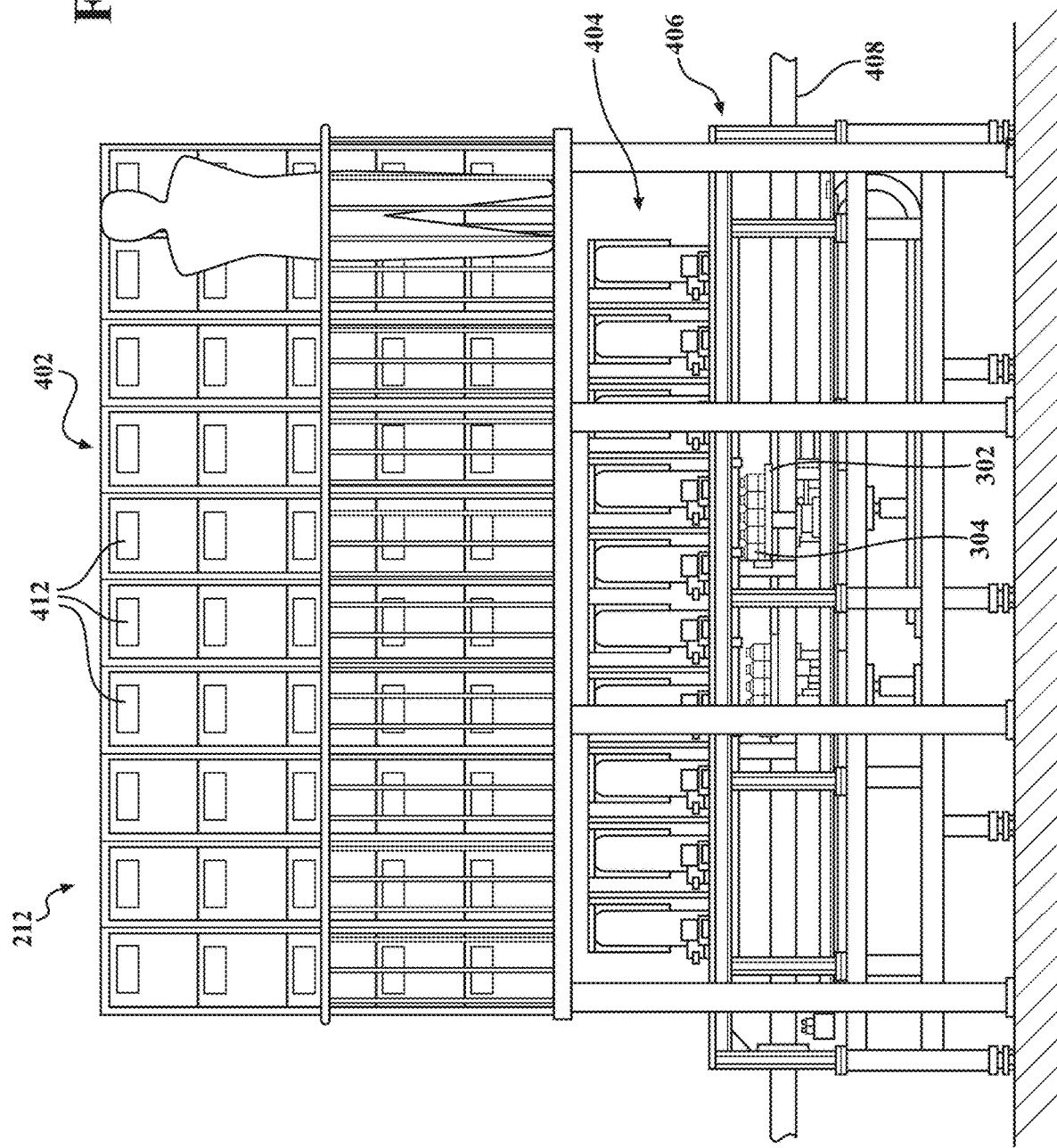
FIG. 5 is a front elevation view of the unit of use device of FIG. 4.

FIG. 4 illustrates the automated dispensing device 212, according to an example embodiment. The automated dispensing device 212 enables dispensing of a number of different types of pharmaceuticals in an automated or semi-automatic manner. The automated dispensing device 212 includes a filling cabinet 402, a prefill assembly 404, and a pallet system 406, which includes a pallet conveyor 408. The filling cabinet 402 stores pharmaceuticals to be dispensed into containers via the prefill assembly 404 and dispenses measured quantities of pharmaceuticals into the prefill assembly 404. The prefill assembly 404 stores the measured quantities of medications 1000 (shown in FIG. 10) and dispenses the measured quantities of medications 1000 received from the filling cabinet 402 into containers 304 on the pallet 302 while the pallet 302 is positioned in the pallet system 406. The pallet conveyor 408 can transport the pallets through some or all of the devices within the pharmacy fulfillment device 112 (shown in FIG. 2).

As discussed in further detail below, in operation, the pallet conveyor 408 automatically brings a pallet 302 (shown in FIG. 3) with one or more containers 304 to the pallet system 406. The pallet system 406 automatically guides the pallet 302 to a location directly beneath the prefill assembly 404 so that the measured quantity of medications 1000 (shown in FIG. 10) can be dispensed into one of the containers 304 found on the pallet 302. This process can be repeated to dispense multiple measured quantities of the same or different medications 1000 into different containers 304 on the pallet 302. The pallet conveyor 408 may be a chain conveyor or a belt driven conveyor, e.g., a belted Bosch TS2 belt-driven conveyor. In some embodiments, the pallet conveyor 408 is a low friction, high-speed conveyor. Although pallets 302 are generally described herein as employed to move a group of containers 304 through the system 100 or within the automated dispensing device 212, trays or other types of carriers and any suitable type of container management system may be employed to individually or as a group move the containers 304 through the system 100 or within the automated dispensing device 212.

In the exemplary embodiment, the filling cabinet 402 is physically adjacent to the prefill assembly 404, and the prefill assembly 404 is physically located directly above the pallet system 406. For example, the filling cabinet 402 and prefill assembly 404 may be located on a second floor (e.g., in a building), and the pallet system 406 may be located on a second floor below the first. These components of the automated dispensing device 212 may be otherwise positioned, e.g., in a position to utilize gravity to move medications 1000 from the filling cabinet 402 to the prefill assembly 404 and then to the containers 304 on the pallet 302. For example, some portion of the filling cabinet 402 may extend below the first floor.

In the exemplary embodiment, the filling cabinet 402 includes multiple cells 412 arranged in a grid-like pattern with a plurality of columns and a plurality of rows. Specifically, in the exemplary embodiment, the filling cabinet 402 has ten columns and nine rows for a total of ninety cells 412. In some embodiments, the filling cabinet 402 has either more or fewer rows and/or columns of cells 412. The various cells 412 may each be adapted to similar or different solid medications 1000 (shown in FIG. 10), e.g., pills, tablets, or capsules. For example, in some embodiments, a commonly prescribed medication 1000 may occupy more than one cell 412. The cells 412 are be adapted to receive inserts 414, which can hold the medications 1000 then automatically dispense the medications 1000 into the prefill assembly 404. In the exemplary embodiment, at least some inserts 416 may be permanently located in the cells 412 (other cells may include inserts that can pull out like drawers). In the exemplary embodiment, only a single filling cabinet 402 with a single prefill assembly 404 is shown. However, in some embodiments, two opposing filing cabinets 402 and two opposing prefill assemblies 404 may be positioned over the same pallet system 404.

Figure 6:
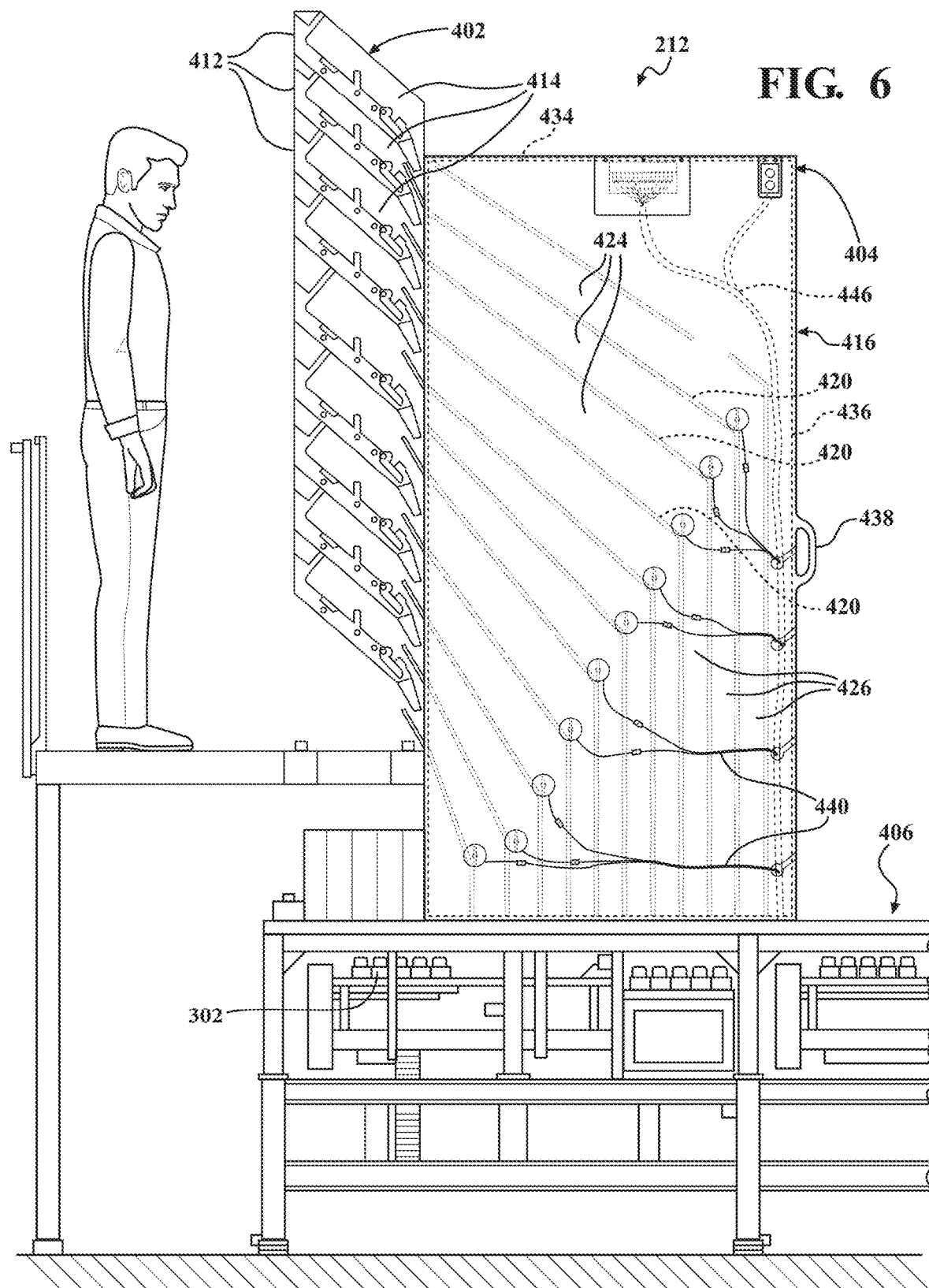
FIG. 6 is a side elevation view of the unit of use device of FIG. 4.
Figure 7:
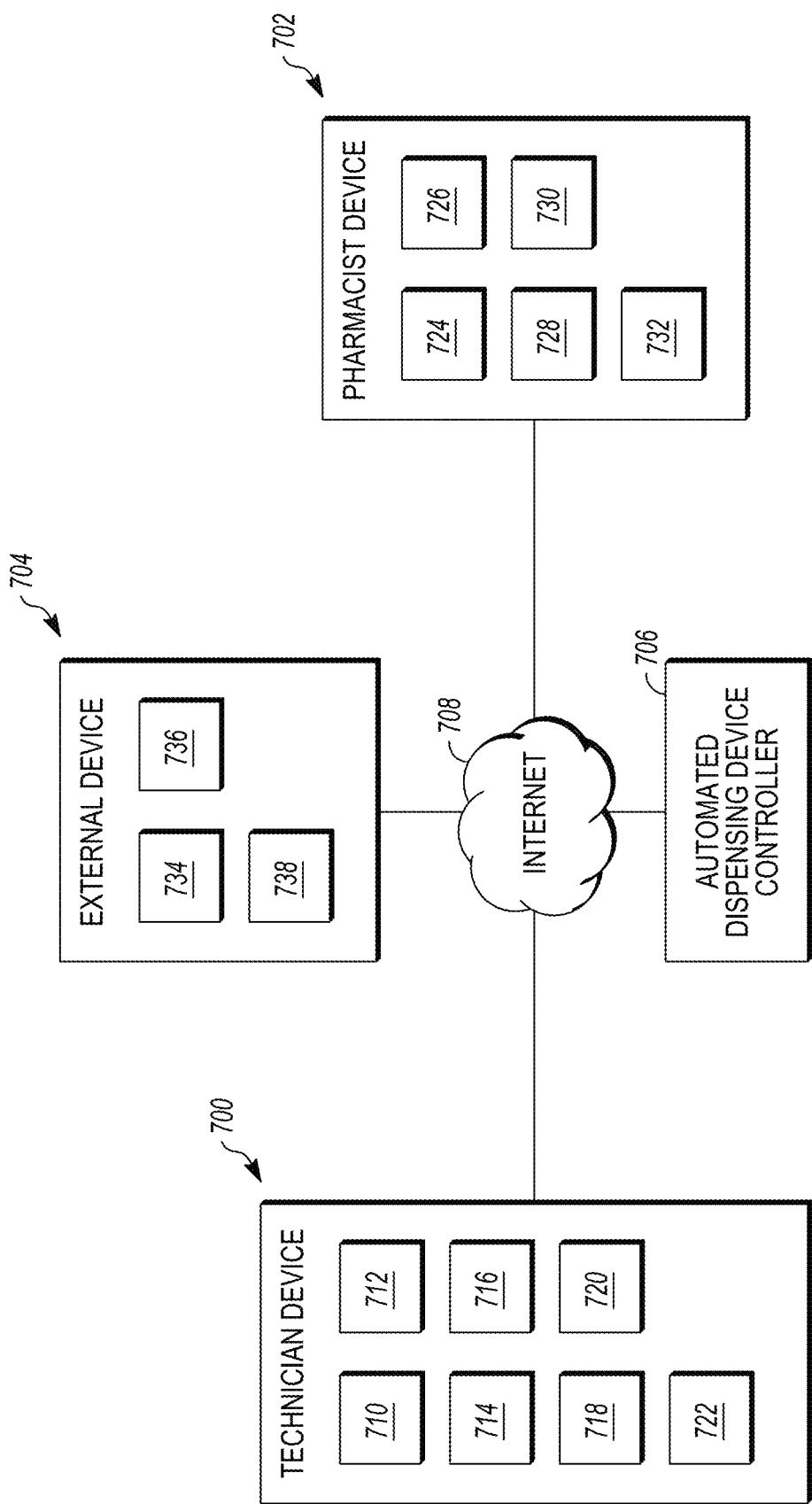
FIG. 7 is a schematic view illustrating a medical verification system.

As shown in FIG. 6, each cell 412 has a pill counter with an output, which feeds the pharmaceuticals contained therein into the prefill assembly 404. The prefill assembly 404 includes a plurality of doors 416 (one being shown), each of which includes a guiding system for guiding the pharmaceuticals dispensed from the respective cells 412 into the appropriate containers 304 on the pallet 302 in the pallet system 406. The doors 416 can be slid horizontally away from the filling cabinet 402 for maintenance either while the automated dispensing device 212 is in operation or shut down. The filling cabinet 402 is configured such that the cell 412 will not dispense medications 1000 (shown in FIG. 10) when the door 416 aligned that cell 412 is out of position, such as during maintenance.

In the exemplary embodiment, each cell 412 has a face plate with a door 416 which must be unlocked to open so that the insert 414 can be filled with medications or so the insert 414 can be replaced with another insert 414. The door 416 is configured to only unlock pursuant to a medication verification process that both mitigates risk of access to the medications 1000 to unauthorized individuals and that mitigates the risks that improper and/or defective medications 1000 will be added to the insert 414. The lock on the door 416 can be of any suitable type which can be remotely and electronically locked and unlocked, for example, with an electronically activated solenoid.

Figure 8:
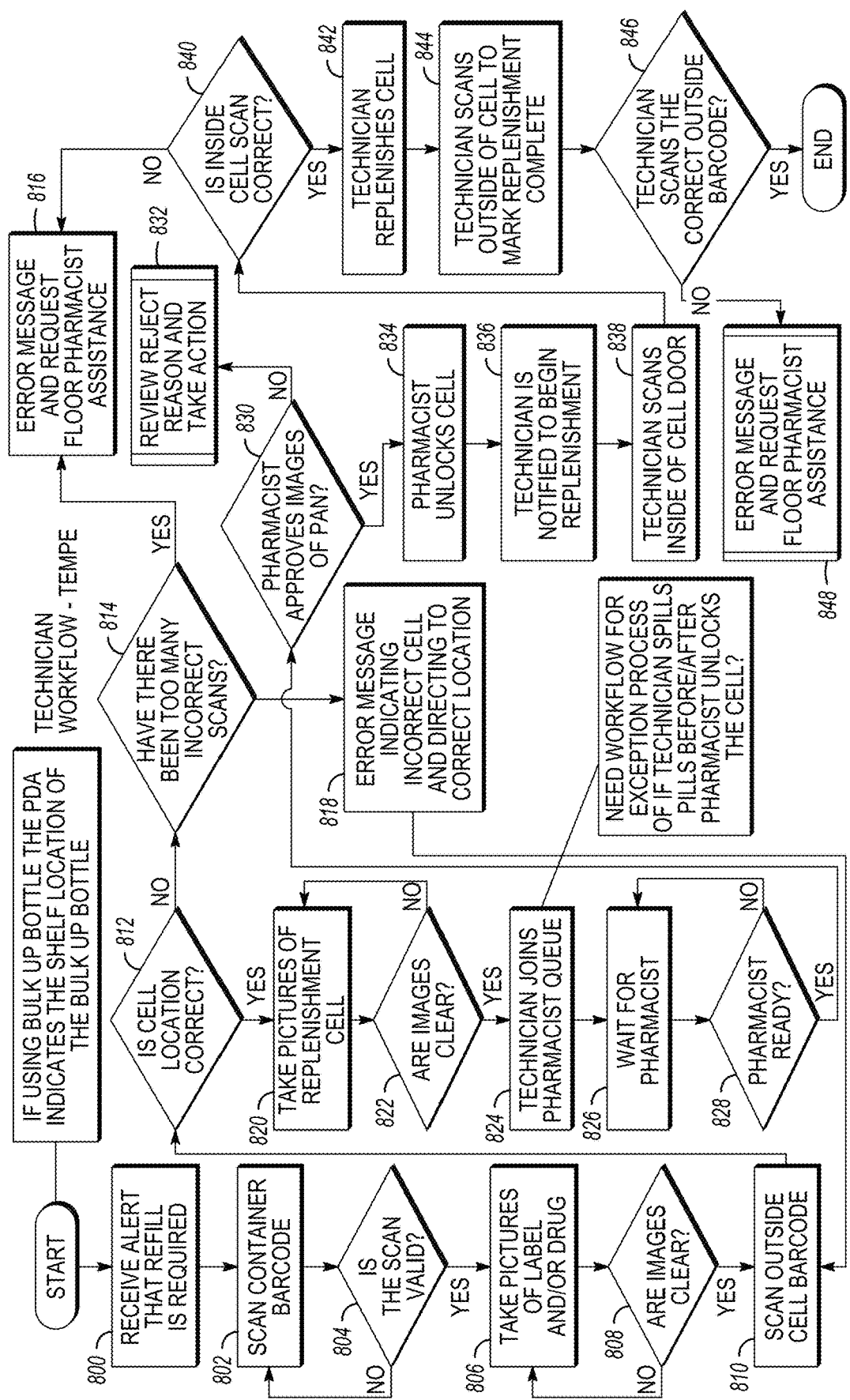
FIG. 8 is a flow chart illustrating the steps pertaining to a technician in a medical verification process.
Figure 12:
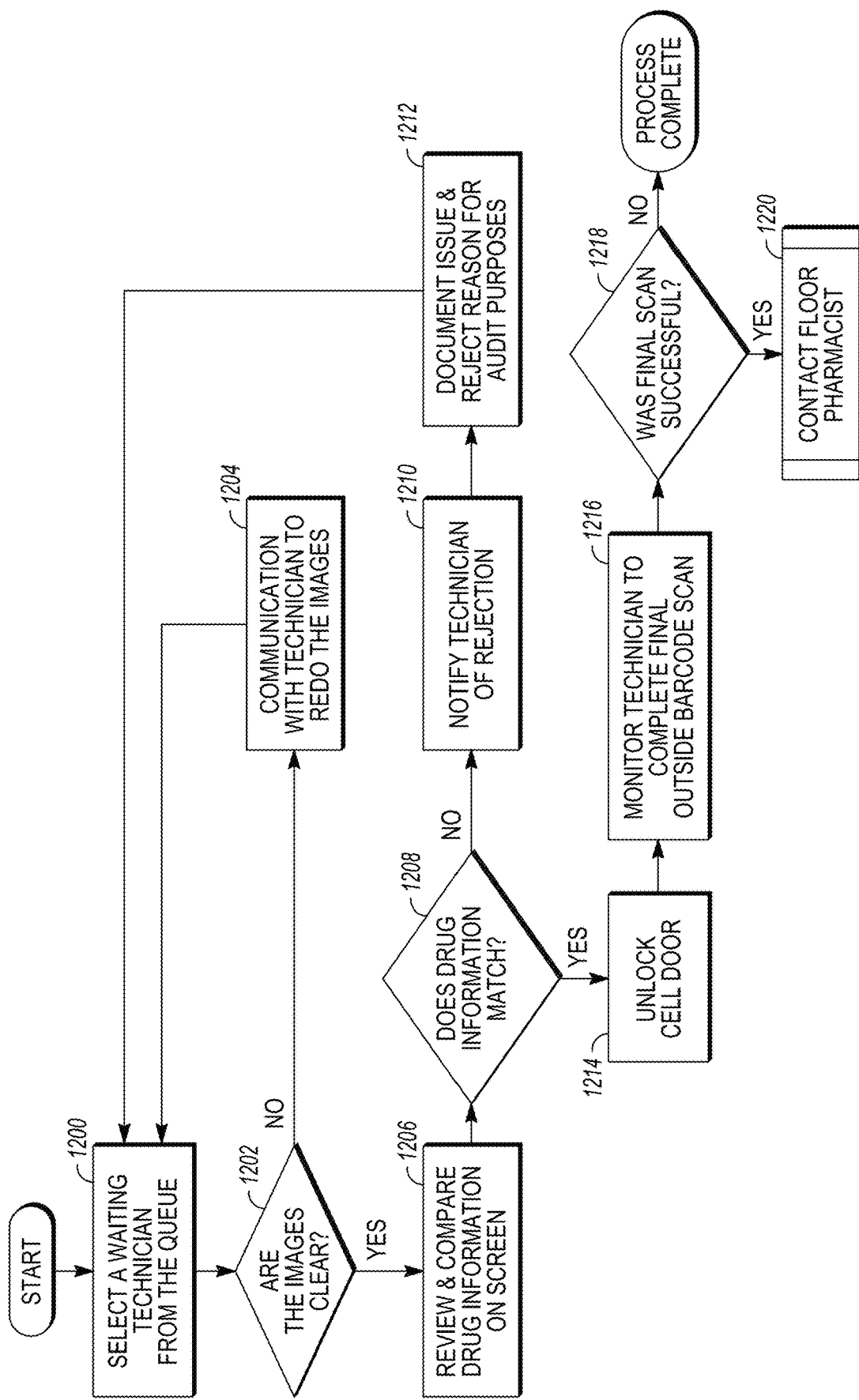
FIG. 12 is a flow chart illustrating the steps pertaining to a pharmacist in the medical verification process.

The medication verification process utilizes at least one technician and a pharmacist. The technician is physically located at the automated dispensing device 212 with the filling cabinet 402 for physically refilling the cells 412 with the medications 1000, and the pharmacist may either be located at the automated dispensing device 212 or who may be remote therefrom. In some embodiments, the automated filling device 212 includes a plurality of filling cabinets 402 and a plurality of technicians with each technician being individually responsible for one or more filling cabinets 402. In other embodiments, more than one technician may be responsible for the same filling cabinet 402. As discussed in further detail below, during the medication verification process, a number of checks must be passed before any medications 1000 can be added to a cell 412, and to overcome those checks, the technician and pharmacist work as a team while utilizing automatic technological tools to ensure that the cells 412 are only filled with the correct medications 1000. The flow charts of FIGS. 8 and 12 illustrate the various steps of the refilling operation with FIG. 8 illustrating the steps pertaining to the technician and FIG. 12 illustrating the steps pertaining to the pharmacist.

Referring now to FIGS. 4, 5, 7, and 10, the technician has a technician device 700; the pharmacist has a pharmacist device 702. The technician device 700 and pharmacist device 702 are in communication with one another, with an external device 704 (such as a server), and with a controller 706 in the automated dispensing device 212 via the internet 708. In operation, the controller 706 continuously monitors the quantities of medications 1000 in the cells 412 of the various filling cabinets 402 within the automated dispensing device 212 and also future demand for medications 1000 based on the types of medications to be added to the containers 304 upstream of the automated dispensing device 212. Based sends an alert to the technician device 700. When the medication count in one of the cells 412 falls below a predetermined threshold, the controller 706 automatically sends a notification signal to the technician device 700.

The technician device 700 is a portable unit, such as a handheld touch computer, a tablet computer, or smart glasses. The technician device 700 includes a display screen 710, which may be, for example, a liquid crystal display (LCD) type of screen or a light emitting diode (LED) type of screen. The technician device 700 also has an input means 712 may include, for example, a touch screen, a stylus, a keyboard, a microphone, and/or an external controller. The technician device 700 further includes an imager 714, which could either be either a built-in camera or an external (for example, wearable) camera. The imager 714 can which communicates wirelessly with a base unit of the technician device 700. The imager 714 can form visible images of a target location, e.g., a part of an automated filling device. The imager 714 can form images using radiation in the humanly visible spectrum e.g., red to blue radiation spectrum. In an example embodiment, the imager 714 can also form images in the non-visible spectrum. The non-visible spectrum can be converted to a visible spectrum for display on a reviewer's device (e.g., a pharmacist display). The imager 714 can form the images and, in the case of photographs, indirectly using an imaging integrated circuit and image processing circuitry, e.g., a DSP. The technician device 700 also includes a processor 716, and a memory 718 operably coupled to the processor, and a portable power source 720, such as a battery or a fuel cell. The technician device 700 includes a wireless module 722, which allows the technician device 700 to access wirelessly a global communication network, e.g., the internet 708 and/or a local network. In some embodiments, the wireless module 722 communicates with the internet 708 via Wi-Fi protocols, Bluetooth® protocols, and/or a cellular network. Other wireless protocols and systems may be used.

The pharmacist device 702 may be either portable or stationary, e.g., a desktop computer, a laptop computer, a handheld touch computer, a tablet computer, or smart glasses. The pharmacist device 702 includes a display screen 724 (such as an LCD or LED display) and includes at least one input means 726 (such as a touch screen, a keyboard, a mouse, a stylus, a microphone, etc.). The pharmacist device 702 includes either a wired and/or wireless module 728, which allows the pharmacist device 702 to access the internet. In some embodiments, the wired or wireless module 728 communicates with the internet and/or the local network via an Ethernet cord, Bluetooth® protocols, and/or a cellular network. The pharmacist device 702 also includes a processor 730 and a memory 732 and, optionally, a power source.

The external device 704 is preferably a server that includes a processor 734, a memory 736, and a wired and/or wireless module 738. In operation, all pictures and information processed by the technician and pharmacist devices 700, 702 along with date and time stamps are saved on the memory 736 of the external device 704 for a predetermined period of time to provide an easily accessible record of all replenishments of the medications 1000 contained within the automated dispensing device 212. The external device 704 may be in the same location as the automated dispensing device 212 or may be located remote therefrom.

In an example embodiment, the external device 704 can perform an image matching process to match the image received from the imager 714 on the technician device 700 to images corresponding to the medication loaded into the automated filling machines. The images corresponding to the medication can be validated images stored in memory in the external device 704. The external device 704 can automatically verify the image from the imager, in an example embodiment, using imaging matching schemes, e.g., template matching, feature matching, point feature matching, and the like, which can be run in the processing circuitry. The external device 704 can highlight on the image file any non-matching elements in the image and send an altered (e.g., highlighted) version of the image file to the pharmacist device 702 for display thereon. The highlighted differences can operate to assist in calling attention to the differences in the image when on the display.

As discussed in further detail below, in operation, the controller 706, the technician device 700, the pharmacist device 702, and the external device 704 all communicate electronically with one another via the internet 708 or a local network to ensure that the medications 1000 in the automated dispensing device 212 are timely replenished so that there is minimal (if any) delay in the dispensing of medications 1000 from the automated dispensing device 212 into the containers 304 being moved through the automated dispensing device 212 by the pallet system 406.

FIG. 8 depicts a flow chart that illustrates the steps pertaining to the technician during the aforementioned process of replenishing one of the cells 412 in the automated dispensing device 212. At step 800, the technician receives a notification on a the pharmacist device 700 that the quantity of medications 1000 in one of the cells 412 is less than a predetermined threshold such that replenishment is required. The technician then finds a container 900 (such as a bulk container or a detrash pan) which contains a known quantity of the medication 1000 contained in the cell 412. At step 802, the technician scans a machine-readable code (such as a barcode, QR code or the like) on a label of the container 900 using the imager 714 or a separate scanning device on the technician device 700.

Figure 9:
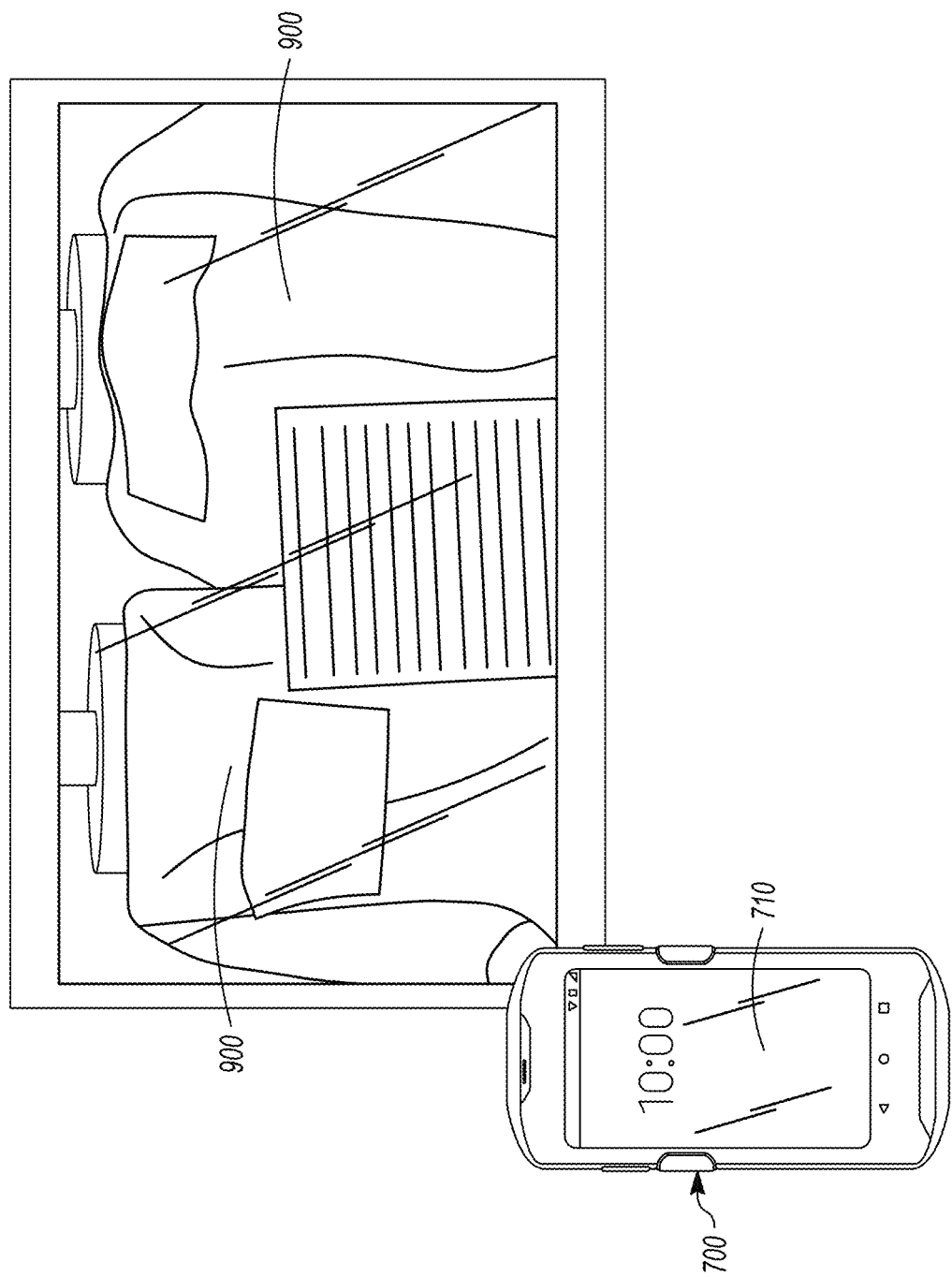
FIG. 9 is a perspective view showing a technician device scanning a container.

FIG. 9 illustrates a technician-performing step 802. At decision step 804, the technician device 700 or the external device 704 determines if the scan of the code is both recognized and valid, i.e., matches the code associated with a known type of medication 1000. If the answer at decision step 804 is no, then the method returns to step 802. If steps 802 and 804 are repeated a predetermined number of times (for example, five), then the technician moves to a different container 900 and repeats step 802. The container 900 may then be moved to a re-evaluation area to determine why it was unable to be scanned.

Figures 10, 11:
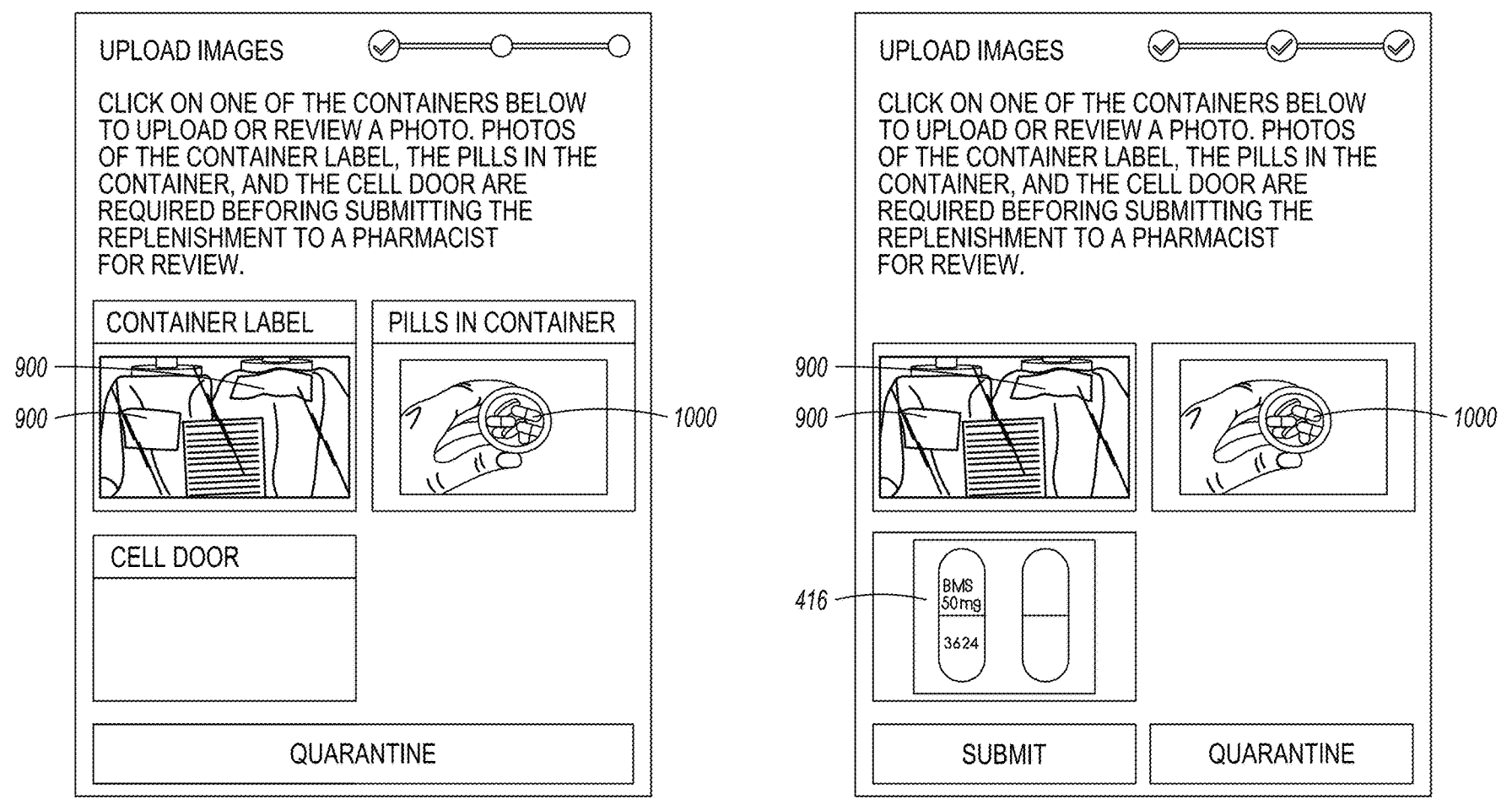

If the answer at decision step 804 is yes, then at step 806, the technician takes a picture of the label on a medication container 900 and a separate picture of the medications 1000 contained in the container 900 using the imager 714 on the technician device 700. The technician may transfer the medications 1000 from the container to a temporary separate container (such as a clear bag) prior to taking the picture of the medications 1000. If step 806 is returned to (discussed below), then potentially only one of these pictures will be taken rather than both. As shown in FIG. 10, the technician device 702 automatically displays the pictures of the container 900 and the medication 1000 in a first graphical user interface (GUI). Thus, the technician can view the pictures that were taken. At decision step 808, the technician determines if the images of the container 900 and the medications 1000 are adequately clear for submission to the pharmacist. If the answer at decision step 808 is no, then the method returns to step 806, and the technician taps whichever one of the container 900 and medications 1000 pictures displayed on the first GUI is not clear and takes a new picture using the imager 714 of the technician device 702. Steps 806 and 808 are repeated until the technician determines that both of these pictures are sufficiently clear for submission to the pharmacist.

If the answer at decision step 808 is yes, then at step 810, the technician scans a code and/or a label on the front of the door 416 of the cell 412 to be replenished. In the exemplary embodiment, each of the doors 416 has a label, which shows the medication 1000 contained therein looks like. However, in some embodiments, other types of codes or labels may be disposed on the outside of the door 416, e.g., text, a Quick-Response (QR) code, or a barcode. At decision step 812, the technician device 702 or the external device 704 automatically determines if the cell 412 that was scanned is the correct cell 412 to be replenished.

If the answer to decision step 812 is no, then at decision step 814, the technician (or an external device) determines if the scan at step 810 has been performed above a predetermined number of times (for example, three). If the answer at decision step 814 is yes, then the process continues to step 816. At step 816, an error message is displayed on the technician device 702, and a local pharmacist is automatically called for direct assistance to troubleshoot the error. If the answer at decision step 814 is no, then at step 818, an error message is displayed on the display screen 710 of the technician device 702 indicating the error and directing the technician to the correct location of the cell 412 to be replenished. The process then proceeds back to step 810.

If the answer at decision step 812 is yes, then the process proceeds to step 820. At step 820, the technician takes a picture of the cell 412 to be replenished using the imager 714 on the technician device 702. As show in FIG. 11, the technician device 702 automatically displays the picture of the cell 412 in the first GUI. At decision step 822, the technician determines if the image of the cell 412 is clear. If the answer at decision step 822 is no, then the technician taps the picture of the cell 412, and the method returns to step 820.

At any time from steps 806, when the technician first sees the medications 1000, through step 822, if the technician notices anything amiss (for example, a problem with the medications 1000 or with the cell 412), then the technician can select a "Quarantine" option on the first GUI. This will alert the system of the potential problem and will call a local pharmacist to provide assistance. The medications 1000 may then be removed from the refilling area and analyzed. The medications 1000 can then be recertified or discarded.

If the answer at decision step 822 is yes, then the technician selects a "Submit" option on the first GUI, and process proceeds to step 824. At step 824, the technician joins a pharmacist queue (discussed in further detail below) and waits for a remote pharmacist to approve the pictures, thereby confirming that the container 900, the medications 1000, and the cell door 416 all match. At steps 826 and 828, the technician device 700 remains in a loop until the pharmacist is ready to review the pictures. Specifically, at step 826, the technician device 700 waits a predetermined period of time, and at decision step 828, it is determined if the pharmacist is ready. If the answer to step 828 is no, then the process proceeds back to step 828. Steps 826 and 828 repeat until the answer to decision step 828 is yes, at which point the process proceeds to decision step 830. At decision step 830, the pharmacist determines if the pictures of the container 900, the medications 1000, and the door 416 are approved. Further details pertaining to this approval process are discussed in further detail below, with reference to FIG. 12.

If the answer to decision step 830 is no, then the process proceeds to step 832. At step 832, the refilling operation is rejected. Following action could include, for example, removing the medications 1000 from the automated dispensing device 212 area for further analysis. The medications 1000 can then be either recertified or discarded. A pharmacist or mechanic may also investigate the cell 412 for problems. If the answer to decision step 830 is yes (i.e., the pharmacist approves the technician's pictures), then the process proceeds to step 834.

At step 834, the pharmacist unlocks the door 416 to the cell 412 using the pharmacist device 702, i.e., a signal is sent from the pharmacist device 702 to the controller 706 to unlock the cell door 416. At step 836, a notification is sent to the technician device 700 that the cell 412 has been unlocked. The alert may be, for example, provided on the display screen 700 of the pharmacist device 700. The technician then has a predetermined amount of time (for example, ten seconds) to proceed to steep 838 and open the door 416 of the cell 412 and scan a code (e.g., a barcode or a QR code) on an inside of the door 416 using the camera 714 or a separate scanner of the technician device 700. If the technician fails to open the door 416 prior to the unlocked period of time expiring, then the technician can request the pharmacist to re-unlock the door 416 through the technician device 700.

After step 838, the process proceeds to decision step 840 where the technician device 700 or the external device 704 automatically compares the scanned code to the code associated with the medication 1000 to be refilled to determine if the code scanned at step 838 was correct. If the answer at decision step 840 is no, then the method proceeds to step 816. At step 816, an error message is displayed on the display screen 710 of the technician device 700, and a local pharmacist is automatically called for direct assistance. If the answer at decision step 840 is yes, then the process proceeds to step 842.

At step 842, the technician empties the contents of the container 900 into the cell 412. At step 844, the technician closes the door 416 and scans or photographs the label on the outside of the door 416, thereby marking the replenishment completed. At decision step 846, the technician device 700, the pharmacist device 702, or the external device 704 determines if the correct cell 412 was scanned at step 844. If the answer to decision step 846 is no, then the process continues to step 848, and an error message is displayed on the display screen 710 of the technician device 700 and a local pharmacist is automatically called to investigate. If the answer to decision step 846 is yes, then the refilling operation ends. The technician may then begin a new refilling operation for a different medication in a different cell of the automated dispensing device 212.

In the exemplary embodiment, during the entire replenishment operation from step 800 to step 846, the technician and the technician device are restricted to only replenishing a single cell 412. Also, during the replenishment operation, all of the photographs and scans are uploaded from the technician device 700 to a database maintained in the external device 704 along with time stamps and an identification of which technician performed the replenishment operation for long term storage. Thus, in the unlikely event that an error is discovered later on, the cause of the error can potentially be diagnosed using the information saved to the database.

Referring now to FIG. 12, a flow chart illustrating the steps pertaining to the pharmacist during the aforementioned process of replenishing one of the cells 412 of the automated dispensing device 212 with medications 1000. At step 1200, a second GUI (such as the one shown in FIG. 12) containing a queue of one or more technicians who are all awaiting the pharmacist's approval is displayed on the display screen 724 of the pharmacist device 702, and the pharmacist selects one of the technicians. The second GUI may organize the technicians in the queue according to a priority metric (e.g., a priority score) which may be based on a number of factors including the current medication counts in the cells 412 to be refilled, the time until more of the medication will be demanded by the automated dispensing device 212 (based on known upcoming dispensing events), and the length of time that the technician associated with that refill has been waiting. In the exemplary embodiment, the priority score is on a 1-10 scale with 1 being the highest priority and 10 being the lowest. In some embodiments, other priority scales are used. The second GUI may also identify which cells 412 are in the queue, the times that the technicians have been waiting for the pharmacist, and the medications 1000 waiting to be filled.

Figure 14:
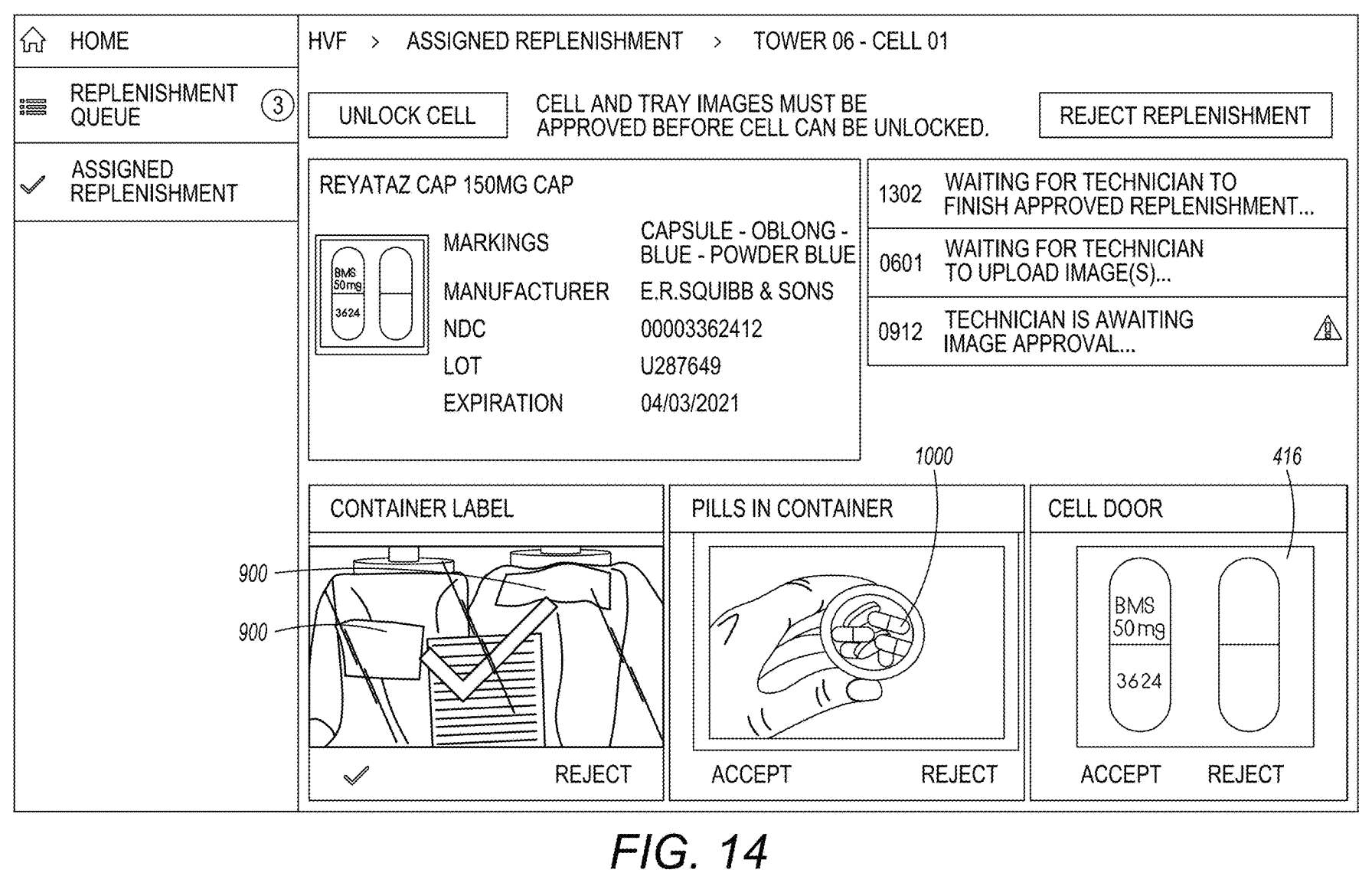

After the pharmacist selects one of the technicians from the second GUI, then a third GUI is displayed on the display screen 724 of the pharmacist device 702. An example third GUI is shown in FIG. 14. In the exemplary embodiment, the third GUI identifies the location of the cell 412 to be replenished and the type of medication 1000 assigned to that cell 900. The third GUI also displays the three pictures taken by the technician, namely, the pictures of the container 900, the medications 1000, and the label on the cell door 416. Adjacent each of these pictures are selectable options "Accept" and "Reject". Further, the third GUI has a "Reject Replenishment" option which can be selected by the pharmacist at any time and an "Unlock Cell" option which only becomes selectable once the pharmacist has confirmed the clarity of all of the pictures. At decision step 1202, the pharmacist determines if the three pictures are sufficiently clear for the pharmacist to confirm that the correct medication has been chosen by the pharmacist. If the answer to decision step 1202 for any of the pictures is no, then at step 1204, the pharmacist communicates the rejection of that picture to the technician by selecting the "Reject" option.

If the answer at decision step 1202 is yes, then at step 1206, the pharmacist reviews the medication information that is associated with the cell 412 and compares that medication information to the three pictures taken by the technician. At decision step 1208, the pharmacist determines if the three pictures all match the medication 900 that is assigned to the cell 412. The pharmacist can confirm this information by selecting "Accept" for each of the pictures on the third GUI.

If the answer at decision step 1208 is no (the pictures do not match the correct medication information), then at step 1210, the pharmacist notifies the technician of the rejection. The pharmacist can process this rejection by selecting the "Reject Replenishment" option in the third GUI. At step 1212, the pharmacist documents the reason for the rejection using the pharmacist device 702, and that reason is stored in the database maintained in the memory 736 of the external device 704. The process then returns to aforementioned step 1200. The medication 1000 may then be removed from the filling area and analyzed before either being recertified or discarded.

If the answer at decision step 1208 is yes, then at step 1214, the pharmacist selects the "Unlock Cell" option from the third GUI. This will allow the technician to open the cell door 416 and replenish the cell 412 with the medications from the container 900. At step 1216, the pharmacist waits for the technician to complete replenishment of the cell 412 and conduct the final scan of the label on the outside of the door 412 (see step 844 of FIG. 8). At decision step 1218, the pharmacist determines if the final scan was successful. If the answer to decision step 1218 is no, then at step 1220, the pharmacist contacts a floor pharmacist at the automated dispensing device 212 to conduct an investigation. If the answer at decision step 1218 is yes, then the pharmacist's job for this replenishment operation is completed. The pharmacist may return to step 1200 to begin another replenishment process.

The refilling operation allows a single pharmacist to be responsible for the approval of a greater number of cells 412 in the automated dispensing device 212 than if the pharmacist must conduct the replenishment operation on his or her own on location at the automated dispensing device 212 while also reducing the risk of a faulty medication replenishment.

Figure 15A:
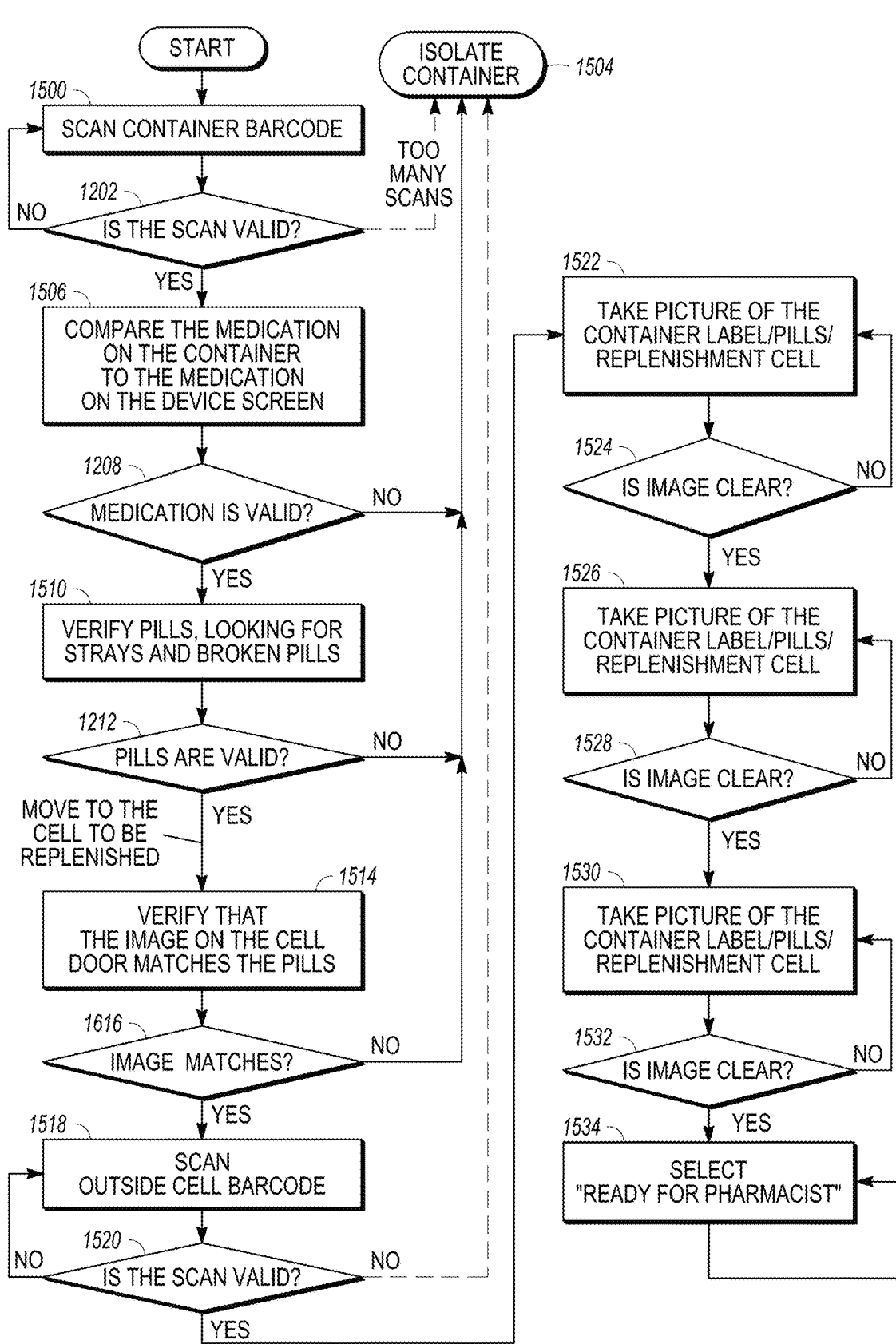
FIGS. 15A and 15B combine to show another flow chart illustrating the steps in a medical verification process.
Figure 15B:
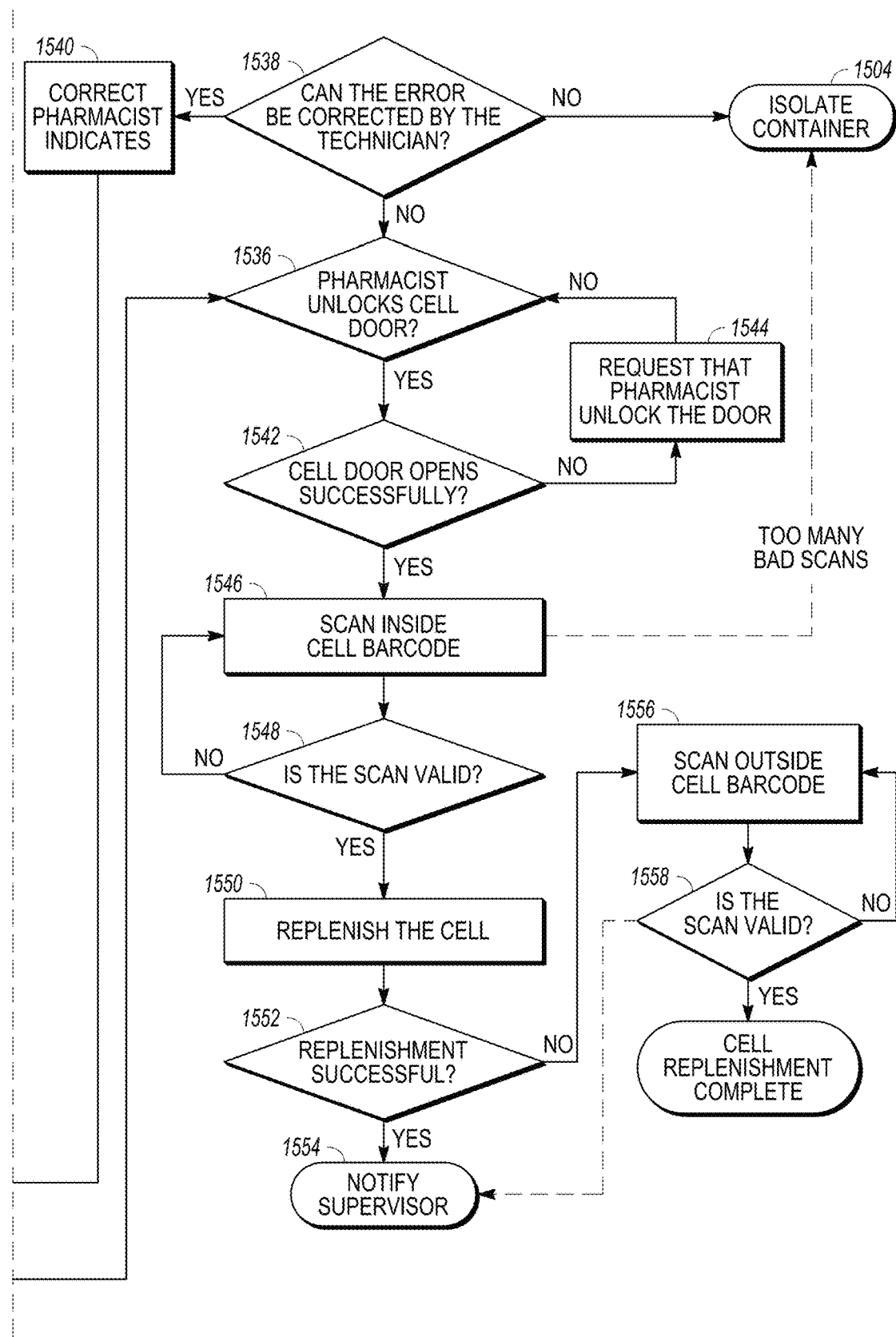

Referring now to FIG. 15, a flow chart depicting an alternate process for replenishing a cell in an automated dispensing device is shown. At step 1500, the technician scans a code on the label on the container 900 with the technician device 700. At decision step 1502, the technician device 700 or the external device 704 automatically determines if the scan of the container 900 was valid. If the answer at decision step 1502 is no, then the process proceeds back to step 1500. If step 1500 has been performed more than a predetermined number of times (for example, five), then the process proceeds to step 1504, and the container 900 is isolated. The medications 1000 in the container 900 may then either be recertified or they may be disposed of. If the answer at decision step 1502 is yes, then the process proceeds to step 1506.

At step 1506, the display screen 710 of the technician device 700 automatically displays information associated with the medication associated with the scanned code on the label, and the technician compares the medication 1000 with the medication information on the display screen 710. At decision step 1508, the technician determines if the medication is valid. If the answer at step 1508 is no, then the process proceeds to step 1504, and the container 900 is isolated. If the answer at decision step 1508 is yes, then the process proceeds to step 1510.

At step 1510, the technician analyzes the medications 1000 in the container 900 for validity. Specifically, the technicians searches the container 900 for stray incorrect medications and for broken medications. At decision step 1512, the technician determines if the medications 1000 are valid. If the answer at decision step 1512 is no, then process proceeds to step 1504, and the container 900 is isolated. If the answer at decision step 1512 is yes, then the method proceeds to step 1514.

At decision step 1514, the technician moves to the cell 412 to be replenished and verifies that the image on the label on the cell door 416 matches the medications 1000. At decision step 1516, the technician determines if the image on the cell door 416 matches the medications 1000. If the answer at decision step 1514 is no, then the process proceeds to step 1504, and the container 900 is isolated. If the answer at decision step 1516 is yes, then the process proceeds to step 1518.

At step 1518, the technician scans the label on the outside of the cell door 416 with the technician device 700. At decision step 1520, the technician device 700 or the external device 704 determines if the scan is valid. If the answer at decision step 1520 is no, then the process returns to step 1518. After a predetermined number of invalid scans (for example, five), then the process proceeds to step 1504, and the container 900 is isolated. If the answer at decision step 1520 is yes, then the process proceeds to step 1522.

At step 1522, the technician takes a picture of one of the container 900, the medications 1000, and the cell door 416 using the technician device 700. At decision step 1524, the technician determines if the picture taken at step 1522 is clear. If the answer at decision step 1524 is no, then the method proceeds back to step 1522. If the answer at decision step 1524 is yes, then the method proceeds to step 1526. At step 1526, the technician takes a picture of a second one of the container 900, the medications 1000, and the cell door 416 using the technician device 700. At decision step 1528, the technician determines if the picture taken at step 1526 is clear. If the answer at decision step 1528 is no, then the process proceeds back to step 1526. If the answer at decision step 1528 is yes, then the process proceeds to step 1530. At step 1530, the technician takes a picture of the remaining one of the container 900, the medications 1000, and the cell door 416 with the technician device 700. At decision step 1532, the technician determines if the picture taken at step 1530 is clear. If the answer at decision step 1532 is no, then the process proceeds back to step 1530. If the answer at decision step 1532 is yes, then the process proceeds to step 1534.

At step 1534, the technician selects an option on the technician device 700 to send the pictures taken at steps 1522, 1526, and 1530 to the pharmacist. At decision step 1536, the pharmacist determines whether to unlock the cell 416. If the answer at decision step 1536 is no, then the pharmacist transmits to the technician the reason for the rejection, and the process proceeds to decision step 1538. At decision step 1538, the technician determines if he or she is able to correct the error. If the answer at decision step 1538 is no, then the method proceeds to step 1504, and the container 900 is isolated. If the answer at decision step 1538 is yes, then the process proceeds to step 1540, and the technician corrects the error and contacts the pharmacist. The process then proceeds back to step 1534.

If the answer at decision step 1536 is yes, then the process proceeds to decision step 1542. At decision step 1542, the technician waits for the cell door 416 to open. If the door 416 does not open after a predetermined period of time, then at step 1544, the technician sends a request the pharmacist to unlock the door 416. The request may be, for example, an alert that is displayed on the display screen 724 of the pharmacist device 702. The process then proceeds back to decision step 1536. If the answer at decision step 1542 is yes, then then the process proceeds to step 1546.

At step 1546, the technician opens the cell door 416 and scans a code on an inside of the door 416 with the technician device 700. At decision step 1548, the technician device 700 or the external device 704 automatically determines if the scan of the code on the inside of the cell door 416 is valid. If the answer at decision step 1548 is no, then the process proceeds back to step 1546. If the answer is no more than a predetermined number of times (for example, five), then the process proceeds to step 1504, and the container 900 is isolated. If the answer at decision step 1548 is yes, then the process proceeds to step 1550.

At step 1550, the technician replenishes the cell 416 with the medications 1000 from the container 900. At decision step 1552, the technician determines if the replenishment was successful. If the answer at decision step 1552 is no, then the process proceeds to step 1554, and a supervisor (for example, a pharmacist on location at the automated dispensing device 212) is notified to assist. If the answer at decision step 1552 is yes, then the process proceeds to step 1556.

At step 1556, the pharmacist closes the cell door 416 and scans the code and/or label on the outside of the cell door 416 with the pharmacist device 700. At decision step 1558, the technician device 700 or the external device 704 determines if the scan is valid. If the answer at decision step 1558 is no, then the process proceeds to step 1554, and a supervisor is notified to assist. If the answer at decision step 1558 is yes, then the process is completed.

Implementations of the systems, algorithms, methods, instructions, etc., described herein may be realized in hardware, software, or any combination thereof. The hardware may include, for example, computers, intellectual property (IP) cores, application-specific integrated circuits (ASICs), programmable logic arrays, optical processors, programmable logic controllers, microcode, microcontrollers, servers, microprocessors, digital signal processors, or any other suitable circuit. In the claims, the term "processor" should be understood as encompassing any of the foregoing hardware, either singly or in combination. The terms "signal" and "data" are used interchangeably.

As used herein, the term module may include a packaged functional hardware unit designed for use with other components, a set of instructions executable by a controller (e.g., a processor executing software or firmware), processing circuitry configured to perform a particular function, and a self-contained hardware or software component that interfaces with a larger system. For example, a module may include an application specific integrated circuit (ASIC), a Field Programmable Gate Array (FPGA), a circuit, digital logic circuit, an analog circuit, a combination of discrete circuits, gates, and other types of hardware or combination thereof. In other embodiments, a module may include memory that stores instructions executable by a controller to implement a feature of the module.

Further, in one aspect, for example, systems described herein may be implemented using a special purpose computer/processor may be utilized which may contain hardware for carrying out any of the methods, algorithms, or instructions described herein. The hardware may become a special purpose device when storing instructions, loading instructions, or executing instructions for the methods and/or algorithms described herein.

Further, all or a portion of implementations of the present disclosure may take the form of a computer program product accessible from, for example, a computer-usable or computer-readable medium. The program includes steps to perform, at least, portions of the methods described herein. A computer-usable or computer-readable medium may be any device that can, for example, tangibly contain, store, communicate, or transport the program for use by or in connection with any processor. The medium may be, for example, an electronic, magnetic, optical, electromagnetic, or a semiconductor device. Other suitable mediums are also available.

The above-described embodiments, implementations, and aspects have been described in order to allow easy understanding of the present disclosure and do not limit the present disclosure. On the contrary, the disclosure is intended to cover various modifications and equivalent arrangements included within the scope of the appended claims, which scope is to be accorded the broadest interpretation to encompass all such modifications and equivalent structure as is permitted under the law.

The invention claimed is:

1. A computing system for authorizing automated dispensing, the computing system comprising:
   memory components;
   communication components configured to transmit and receive data communication signals over a network; and
   at least one processor communicatively coupled to the memory components and the communication components, the at least one processor configured to:
   receive scanned code data associated with a first cell of an automated dispensing device, from at least one imaging computing device remotely located from the computing system, via the communication components, wherein the automated dispensing device comprises at least a filling cabinet that includes a plurality of cells associated with items to be dispensed, and wherein the plurality of cells includes the first cell;
   determine that the first cell comprises a correct cell of the filling cabinet to be replenished, based on the scanned code data;
   receive a plurality of images from the at least one imaging computing device, via the communication components, the plurality of images being associated with operation of the automated dispensing device;
   perform a comparison of a first image of the plurality of images to at least a second image comprising a validated image corresponding to the items to be dispensed from the first cell;
   determine whether an item in the first image of an item container comprises a correct item for replenishing the first cell of the automated dispensing device, based on the comparison, wherein the items to be dispensed include the correct item; and
   when the item comprises the correct item, transmit a signal to allow opening of the automated dispensing device for the replenishing of the correct item.

2. The computing system of claim 1, wherein the items comprise solid medications; and
   wherein the solid medications include at least one of: pills, tablets, and capsules.

3. The computing system of claim 1, wherein the at least one processor is further configured to:
   receive a photograph of a door of the first cell of the automated dispensing device from the at least one imaging computing device, wherein the plurality of images includes the photograph of the door; and
   transmit the signal to allow opening of the automated dispensing device upon a positive verification that the photograph of the door shows the first cell.

4. The computing system of claim 1, wherein the second image comprises a stored image of the items to be dispensed from the first cell of the plurality of cells; and
   wherein the stored image indicates the correct item for replenishing the first cell.

5. The computing system of claim 1, wherein the at least one processor is further configured to:
   determine whether the first image and the second image match, based on the comparison, using at least one of template matching, feature matching, and point feature matching; and
   when the first image and the second image match, determine that the item in the first image of the item container comprises the correct item.

6. The computing system of claim 1, wherein the at least one processor is further configured to:
   highlight non-matching elements on an image file for the first image, to generate an altered first image file; and
   perform the comparison based on the altered first image file.

7. The computing system of claim 1, wherein the plurality of cells are locked by a lock that can be electronically activated; and
   wherein allowing opening of the automated dispensing device further comprises:
      transmitting an unlock signal, via the communication components, to unlock the lock of at least the first cell of the plurality of cells, to create at least one unlocked cell for the replenishing of the correct item.

8. The computing system of claim 1, wherein the at least one imaging computing device includes a technician mobile device and is operated by a technician on location at the automated dispensing device; and
   wherein the computing system includes a pharmacist device operated by a pharmacist and at least one server communicatively coupled to the pharmacist device.

9. The computing system of claim 1, wherein the first image comprises a first photograph;
   wherein the computing system further comprises a display component; and
   wherein the computing system is further adapted to display the first photograph of the item container via the display component along with a second photograph of the item associated with the automated dispensing device.

10. The computing system of claim 1, wherein the at least one processor is further configured to:
    receive a second set of scanned code data associated with an open door of the first cell, from the at least one imaging computing device, wherein the second set is scanned inside the first cell;
    perform a second comparison of the second set of scanned code data to a code associated with the items to be dispensed from the first cell;
    determine correctness of the second set of scanned code, based on the second comparison; and
    transmit the signal to allow opening of the automated dispensing device, based on determining the correctness of the second set of scanned code, determining that the first cell comprises a correct cell, and determining that the item comprises the correct item.

11. The computing system of claim 1, wherein the at least one processor is further configured to:
    receive a third set of scanned code data associated with a closed door of the first cell, from the at least one imaging computing device, wherein the third set is scanned outside the closed door;
    determine that the correct cell has been scanned, based on the third set of scanned code data; and
    determine that the replenishing is complete, based on the closed door and the third set of scanned code data.

12. The computing system of claim 11, wherein the at least one processor is further configured to:
    store the third set of scanned code data with corresponding date and time stamps, using at least the memory components, to create a stored record of the replenishing of the items to be dispensed from the first cell; and
    maintain storage of the stored record of the replenishing for a predetermined period of time.

13. A method for authorizing automated dispensing, the method comprising:
    receiving scanned code data associated with a first cell of an automated dispensing device from at least one imaging computing device, by a computing system remotely located from the at least one imaging computing device, wherein the automated dispensing device comprises at least a filling cabinet that includes a plurality of cells associated with items to be dispensed, and wherein the plurality of cells includes the first cell;
    determining that the first cell comprises a correct cell of the filling cabinet to be replenished, based on the scanned code data, by the computing system;
    receiving a plurality of images from the at least one imaging computing device, by the computing system, the plurality of images being associated with operation of the automated dispensing device;
    performing a comparison of a first image of the plurality of images to at least a second image comprising a validated image corresponding to the items to be dispensed from the first cell, by the computing system;
    determining whether an item in the first image of an item container comprises a correct item for replenishing the first cell of the automated dispensing device, based on the comparison, by the computing system, wherein the items to be dispensed include the correct item; and
    when the item comprises the correct item, transmitting a signal to allow opening of the automated dispensing device for the replenishing of the correct item, by the computing system.

14. The method of claim 13, further comprising:
    receiving a photograph of a door of the first cell of the automated dispensing device from the at least one imaging computing device, by the computing system, wherein the plurality of images includes the photograph of the door; and
    transmitting the signal to allow opening of the automated dispensing device upon a positive verification that the photograph of the door shows the first cell.

15. The method of claim 13, further comprising:
    determining whether the first image and the second image match, based on the comparison, by the computing system, using at least one of template matching, feature matching, and point feature matching; and
    when the first image and the second image match, determine that the item in the first image of the item container comprises the correct item.

16. The method of claim 13, further comprising:
    highlighting non-matching elements on an image file for the first image, by the computing system, to generate an altered first image file; and
    performing the comparison based on the altered first image file.

17. The method of claim 13, wherein the plurality of cells are locked by a lock that can be electronically activated; and
wherein allowing opening of the automated dispensing device further comprises:
transmitting an unlock signal, by the computing system via communication components, to unlock the lock of at least the first cell of the plurality of cells, to create at least one unlocked cell for the replenishing of the correct item.

18. The method of claim 13, further comprising:
receiving a second set of scanned code data associated with an open door of the first cell from the at least one imaging computing device, by the computing system, wherein the second set is scanned inside the first cell;
performing a second comparison of the second set of scanned code data to a code associated with the items to be dispensed from the first cell, by the computing system;
determining correctness of the second set of scanned code, based on the second comparison, by the computing system; and
transmitting the signal to allow opening of the automated dispensing device, by the computing system via communication components, based on determining the correctness of the second set of scanned code, determining that the first cell comprises a correct cell, and determining that the item comprises the correct item.

19. The method of claim 13, further comprising:
receiving a third set of scanned code data associated with a closed door of the first cell from the at least one imaging computing device, by the computing system, wherein the third set is scanned outside the closed door;
determining that the correct cell has been scanned, based on the third set of scanned code data, by the computing system; and
determining that the replenishing is complete, by the computing system, based on the closed door and the third set of scanned code data.

20. The method of claim 19, further comprising:
storing the third set of scanned code data with corresponding date and time stamps, by the computing system using memory components, to create a stored record of the replenishing of the items to be dispensed from the first cell; and
maintaining storage of the stored record of the replenishing for a predetermined period of time.

* * * * *